US005855920A

United States Patent [19]
Chein

[11] Patent Number: 5,855,920
[45] Date of Patent: Jan. 5, 1999

[54] TOTAL HORMONE REPLACEMENT THERAPY

[76] Inventor: Edmund Y. M. Chein, 1100 Maytok Pl., Beverly Hills, Calif. 90210

[21] Appl. No.: 766,320

[22] Filed: Dec. 13, 1996

[51] Int. Cl.$^6$ .......................... A61K 35/55; A61K 35/26; A61K 38/00; A61K 31/56; A61K 31/405

[52] U.S. Cl. .......................... 424/568; 424/580; 514/21; 514/171; 514/177; 514/178; 514/182; 514/415

[58] Field of Search .................................. 424/568, 580; 514/21, 171, 177, 178, 182, 415

[56] References Cited

U.S. PATENT DOCUMENTS

| | | | |
|---|---|---|---|
| 4,897,389 | 1/1990 | Aroonsakul | 514/171 |
| 4,898,856 | 2/1990 | Aroonsakul | 514/171 |
| 4,898,857 | 2/1990 | Aroonsakul | 514/171 |
| 4,902,680 | 2/1990 | Aroonsakul | 514/171 |
| 5,017,470 | 5/1991 | Aroonsakul | 435/4 |
| 5,391,381 | 2/1995 | Wong et al. | 424/473 |
| 5,397,771 | 3/1995 | Bechgaard et al. | 514/2 |
| 5,434,146 | 7/1995 | Labrie et al. | 514/169 |
| 5,550,107 | 8/1996 | Labrie | 514/11 |
| 5,563,131 | 10/1996 | Berliner et al. | 514/177 |

OTHER PUBLICATIONS

Advanced Medical Therapy: Human Growth Hormone Replacement Therapy In Adults, Edward M. Lichten, M.D., P.C. (1997).

"Effects Of Human Growth Hormone In Men Over 60 Years Old", Rudman, D.; Feller, A.G.; Nagraj, H.S.; Gergans, G.A.; Lalitha, P.Y.; Goldberg, A.F.; Schlenker, R.A.; Cohn, L.; Rudman, I.W.; Mattson, D.E.; The New England Journal of Medicine, vol. 323, No. 1, Jul. 5, 1990.

"Restoring Ebbing Hormones May Slow Aging", Brody, J.E., Science Times, The New York Times, Tuesday, Jul. 18, 1995.

"Metabolic effects of GH: a rationale for continued GH treatment of GH–deficient adults after cessation of linear growth", Juul A; Jorgensen JO; Christiansen JS; Muller J; Skakkeboek NE, Department of Growth and Reproduction, University of Copenhagen, Denmark. Horm Res (Switzerland) 1995, 44 Suppl 3 pp. 64–72, ISSN 0301–0163 Journal Code: GBI.

"Insulin–like growth factor I alters peripheral thyroid hormone metabolism in humans: comparison with growth hormone", Hussain MA; Schmitz O; Jorgensen JO; Christiansen JS; Weeke J; Schmid C; Froesch ER, Division of Endocrinology and Metabolism, University Hospital of Zurich, Switzerland. Eur J Endocrinol (Norway) May 1996, 134 (5) pp. 563–567, ISSN 0804–4643 Journal Code: BXU.

"Improved final height in girls with Turner's syndrome treated with growth hormone and oxandrolone", Nilsson KO; Albertsson–Wikland K; Alm J; Aronson S; Gustafsson J; Hagenas L; Hager A; Ivarsson SA; Karlberg J; Kristrom B; Marcus C; Moell C; Ritzen M; Tuvemo T; Wattsgard C; Westgren U; Westphal O; Aman J, Department of Pediatrics, University Hospital Malmo, Sweden. J Clin Endocrinol Metab (United States) Feb. 1996, 81 (2) pp. 635–640, ISSN 0021–972X Journal Code: HRB.

"Insulin, insulin–like growth factor–binding protein–1, and sex hormone–binding globulin in patients with Turner's syndrome: course over age in untreated patients and effect of therapy with growth hormone alone and in combination with oxandrolone", Haeusler G; Schmitt K; Blumel P; Plochl E; Waldhor T; Frisch H, Pediatric Department, University of Vienna, Austria. J Clin Endocrinol Metab (United States) Feb. 1996, 81 (2) pp. 536–541, ISSN 0021–972X Journal Code: HRB.

"Growth hormone deficiency in adults: characteristics and response to growth hormone replacement", Lieberman SA; Hoffman AR, Department of Internal Medicine, University of Texas Medical Branch, Galveston 77555–1060, USA. J Pediatr (United States) May 1996, 128 (5 Pt 2) pp. S58–S60, ISSN 0022–3476 Journal Code: JLZ.

"Effect of anabolic hormones and insulin–like growth factor–I on muscle mass and strength in elderly persons", Carter WJ, John L. McClellan Memorial Veterans Hospital, Little Rock, Arkansas, USA. Clin Geriatr Med (United States) Nov. 1995, 11 (4) pp. 735–748, ISSN 0749–0690 Journal Code: CLN.

"Screening for PIT1 abnormality by PCR direct sequencing method", Irie Y; Tatsumi K; Kusuda S; Kawawaki H; Boyages SC; Nose O; Ichiba Y; Katsumata N; Amino N, Department of Laboratory Medicine, Osaka University Medical School, Japan. Thyroid (United States) Jun. 1995, 5(3) pp. 207–211, ISSN 1050–7256 Journal Code: BJW.

(List continued on next page.)

Primary Examiner—Kimberly Jordan
Attorney, Agent, or Firm—Blakely, Sokoloff, Taylor & Zafman, LLP

[57] ABSTRACT

A hormone replenishment method particularly useful in maintaining the body's neuroendocrine clock at optimal levels and combating conditions associated with advancing age is disclosed. The method includes determining that the level of human growth hormone and at least two other supplemental hormones are below optimal or pre-determined physiological levels for an adult human. Once it has been established that the level of human growth hormone and at least two of certain supplemental hormones are below pre-determined physiological levels, the method includes establishing a regimen for the replenishment of the level of the deficient hormones to optimal or pre-determined physiological levels. The supplements hormones include the sex hormones, namely testosterone, progesterone, and estrogen, the pineal hormone melatonin, the adrenal hormones, namely DHEA and pregnenolone, the thyroid hormone, and the thymus hormone. A method of increasing life expectancy and life span by determining the level of human growth hormone and at least two of the supplemental hormones and establishing a regimen for the maintenance of the level of human growth hormone and supplemental hormones at optimal or pre-determined physiological levels is also disclosed.

37 Claims, 13 Drawing Sheets

OTHER PUBLICATIONS

"Trophic factor supplementation: effect on the age–associated changes in body composition", Schwartz RS, University of Washington School of Medicine, Division of Gerontology and Geriatric Medicine, Harborview Medical Center, Seattle, USA. J Gerontol A Biol Sci Med Sci (United States) Nov. 1995, 50 Spec No pp. 151–156, ISSN 1079–5006 Journal Code: CBA.

"Treatment of growth hormone–deficient adults with recombinant human growth hormone increases the concentration of growth hormone in the cerebrospinal fluid and affects neurotransmitters", Johansson JO; Larson G; Andersson M; Elmgren A; Hynsjo L; Lindahl A; Lundberg PA; Isaksson OG; Lindstedt S; Bengtsson BA, Department of Internal Medicine, University of Goteborg, Sweden. Neuroendocrinology (Switzerland) Jan. 1995, 61 (1) pp. 57–66, ISSN 0028–3835 Journal Code: NY8.

"Adult growth hormone deficiency", Jorgensen JO; Muller J; Moller J; Wolthers T; Vahl N; Juul A; Skakkebaek, NE; Christiansen JS, Medical Department M (Endocrinology and Diabetes), Aarhus Kommunehospital, Denmark. Horm Res (Switzerland) 1994, 42 (4–5) pp. 235–241, ISSN 0301–0163 Journal Code: GBI.

"Effects of recombinant human growth hormone on metabolic indices, bodycomposition, and bone turnover in healthy elderly women", Holloway L; Butterfield G; Hintz RL; Gesundheit N; Marcus R, Aging Study Unit, Palo Alto Veterans Affairs Medical Center, California 94304. J Clin Endocrinol Metab (United States) Aug. 1994, 79 (2) pp. 470–479, ISSN 0021–972X Journal Code: HRB.

"Treatment of growth delay in boys with isolated growth hormone deficiency", Albanese A; Stanhope R, Medical Unit, Institute of Child Health, London, UK. Eur J Endocrinol (Norway) Jan. 1994, 130 (1) pp. 65–69, ISSN 0804–4643 Journal Code: BXU.

"Management of the short stature due to pubertal delay in boys", Adan L; Souberbielle JC; Brauner R, Pediatric Endocrinology Unit, Hopital et Faculte Necker–Enfants Malades, Paris, France. J Clin Endocrinol Metab (United States) Feb. 1994, 78 (2) pp. 478–482, ISSN 0021–972X Journal Code: HRB.

"Aging and growth hormone", Ho KK; Hoffman DM, Garvan Institute of Medical Research, St. Vincent's Hospital, Sydney, Australia. Horm Res (Switzerland) 1993, 40 (1–3) pp. 80–86, ISSN 0301–0163 Journal Code: GBI.

"Treatment of adults with growth hormone (GH) deficiency with recombinant human GH", Bengtsson BA; Eden S; Lonn L; Kvist H; Stokland A; Lindstedt G; Bosaeus I; Tolli J; Sjostrom L; Isaksson OG, Department of Medicine, Sahlgrenska Hospital, Medical Faculty, University of Goteborg, Sweden. J Clin Endocrinol Metab (United States) Feb. 1993, 76 (2) pp. 309–317, ISSN 0021–972X Journal Code: HRB.

"Regulation of growth hormone binding protein in man: comparison of gel chromatography and immunoprecipitation methods", Ho KK; Valiontis E; Waters MJ; Rajkovic IA Garvan, Institute of Medical Research, St. Vincent's Hospital, Sydney,NSW, Australia. J Clin Endocrinol Metab (United States) Feb. 1993, 76 (2) pp. 302–308, ISSN 0021–972X Journal Code: HRB.

"Growth hormone therapy in Turner's syndrome. Impact of injection frequency and initial bone age", Rongen–Westerlaken C; van Es A; Wit JM; Otten BJ; De Muinck Keizer––Schrama SM; Drayer NM; Oostdijk W; Delemarre–vd Waal HA; Gons MH;Waelkens JJ; et al, Department of Pediatrics, University of Utrecht, The Netherlands. Am J Dis Child (United States) Jul. 1992, 146 (7) pp. 817–820, ISSN 0002–922X Journal Code: 3GS.

"Nocturnal thyrotropin surge in growth hormone–deficient children", Municchi G; Malozowski S; Nisula BC; Cristiano A; Rose SR, Developmental Endocrinology Branch, National Institute of Child Health and Human Development, National Institutes of Health, Bethesda, Maryland 20892. J Pediatr (United States) Aug. 1992, 121 (2) pp. 214–220, ISSN 0022–3476 Journal Code: JLZ.

ASSESSMENT
EFFECTS OF HUMAN GROWTH HORMONE ADMINISTRATION
(LOW DOSE-HIGH FREQUENCY)
IN 202 PATIENTS'

L. CASS TERRY, M.D., PH.D. & EDMUND CHEIN, M.D., MEDICAL COLLEGE OF WISCONSIN & PALM SPRINGS LIFE EXTENSION INSTITUTE

| STRENGTH, EXERCISE & BODY FAT: | IMPROVEMENT[1] |
|---|---|
| MUSCLE STRENGTH | 88% |
| MUSCLE SIZE | 81% |
| BODY FAT LOSS | 72% |
| EXERCISE TOLERANCE | 81% |
| EXERCISE ENDURANCE | 83% |

| SKIN & HAIR: | |
|---|---|
| SKIN TEXTURE | 71% |
| SKIN THICKNESS | 68% |
| SKIN ELASTICITY | 71% |
| WRINKLE DISAPPEARANCE | 51% |
| NEW HAIR GROWTH | 38% |

| HEALING, FLEXIBILITY & RESISTANCE: | |
|---|---|
| HEALING OF OLD INJURIES | 55% |
| HEALING OF OTHER INJURIES | 61% |
| HEALING CAPACITY | 71% |
| BACK FLEXIBLITY | 53% |
| RESISTANCE TO COMMON ILLNESS | 73% |

| SEXUAL FUNCTION: | IMPROVEMENT[2] |
|---|---|
| SEXUAL POTENCY/FREQUENCY | 75% |
| DURATION OF PENILE ERECTION | 62% |
| FREQUENCY OF NIGHTIME URINATION | 57% |
| HOT FLASHES | 58% |
| MENSTRUAL CYCLE REGULATION | 39% |

| ENERGY, EMOTIONS & MEMORY: | |
|---|---|
| ENERGY LEVEL | 84% |
| EMOTIONAL STABILITY | 67% |
| ATTITUDE TOWARD LIFE | 78% |
| MEMORY | 62% |

[1] MEAN SELF-ASSESMENT TIME WAS 180 DAYS AFTER HGH THERAPY INITIATION; RANGES = 15-720 DAYS.

[2] BASED UPON 308 RESPONSES; RATING IMPROVEMENT AS SLIGHT TO DEFINITE.

Fig. 10

TOTAL HORMONE REPLACEMENT THERAPY

BACKGROUND OF THE INVENTION

1. Field of the Invention

The invention relates to hormone therapy and more particularly to the restoration and balance of a select group of hormones to maintain optimal physiological levels.

2. Description of Related Art

It is known that the levels of a variety of hormones drop substantially with age. These include human growth hormone, sex hormones, pineal, adrenal, thyroid, and thymus hormones. The following sections describe various hormones that decline with age.

A. Human Growth Hormone

One of the hormones that declines sharply with age is human growth hormone (HGH, GH, or somatotropin). FIG. 1 illustrates the growth hormone decline in years for an ordinary human.

HGH is a protein hormone secreted by the somatotropic cells of the anterior lobe of the pituitary gland. HGH secrets in a pulsatile manner throughout a 24-hour period. The pulsatile diurnal output of growth hormone is modulated by a pair of inner synergistic hypothalamus hormones, the growth hormone releasing hormone (GHRH) and growth hormone inhibiting hormone (GHIH) or somatostatin. GHRH and GHIH are synthesized in the hypothalamus and transported along with other messenger hormones to the pituitary gland by means of a short specialized portal vein network. GHRH is essentially a series of short pulses, clocked at about once a minute uniformly throughout a 24-hour day. GHIH, on the other hand, is a "gatekeeper" that is normally high but occasionally low allowing pulses of growth hormone to be released from the pituitary gland into the bloodstream. The base line level of growth hormone, as far as serum concentration is concerned, is ordinarily at or below detectable limits from hour to hour.

The major secretion of HGH occurs at night, one to two hours after the onset of deep REAM sleep. Peek secretion levels are between 10–50 ng/ml.

It is known that physiological roles are probably due both to direct actions of HGH and indirect actions mediated by the peptide hormones known as somatomedins. Somatomedins are stimulated predominantly by the action of HGH and include insulin-like growth factor-I (also known as IGF-I and somatomedin-C) and IGF-II. The major site of somatomedin secretions is the liver, but there is also some production at peripheral sites.

Proper human growth from infancy is contingent upon adequate growth hormone secretion. Growth hormone appears to affect the growth of virtually every organ and tissue in the body. In normal development, HGH and the somatomedins are responsible for many manifestations of normal growth. Growth hormone deficiency during the childhood growing period is manifested by profound short stature. This deficiency has been treated by human growth hormone supplements for many years. However, the scarcity of the source material for natural HGH (i.e., pituitary glands of cadavers) has limited investigations into other possible applications for HGH. Recently, bioengineered HGH or recombinant HGH has been developed with identical characteristics as the natural HGH and removed the previous investigation limitations.

In 1990, a group of researchers published a report that showed that the declining activity of the IGF-I access with advancing age may contribute to the decrease in lean body mass and the increase of mass of adipose tissue that occur with aging. "Effects Of Human Growth Hormone In Men Over 60 Years Old", Rudman, D., M.D., et al., *The New England Journal of Medicine*, Vol. 323, No. 1, Jul. 5, 1990. Subsequent studies have shown that growth hormone increases bone mass in osteoporosis, reverses declining cardiac function, reverses declining pulmonary function, reverses the decline in immune function associated with aging, increases lean muscle mass, decreases the percentage of body fat, and increase the capacity for exercise. See Powrie, J. et al. "Growth Hormone Replacement Therapy For Growth Hormone-Deficient Adults", Drugs Vol. 49, No. 5, pages 656–63, 1995; Rosén, T., et al., "Consequences Of Growth Hormone Deficiency In Adults And The Benefits And Risks of Recombinant Human Growth Hormone Treatment", Horm. Rees., Vol. 43, pages 93–99, 1995; and Hoffman, A. R., "Growth Hormone Therapy In The Elderly: Implications For The Aging Brain", Psychoneuroendocrinology, Vol. 17, No. 4, pages 327–33, 1992 (concluding that it is possible that chronic physiological GH and/or IGH-I replacement therapy might reverse or prevent some of the inevitable sequelae of aging).

Growth hormone replacement therapy has been criticized because of side effects. Reported side affects include fluid retention, which is manifested by peripheral edema, joint swelling, and arthralgias (particularly in the hands), and carpal tunnel syndrome. Some epidemialogical reports suggest also that acromegalic patients have a general increase in the risk of malignancy, especially from colonic cancer and colonic polyps. However, reports of these side effects can be attributed to the method of administration of growth hormone replacement. None of the reports critical of growth hormone replacement report a method of administration consistent with the body's natural secretion of the hormone.

B. Androgens

Androgens are another class of hormones that drop substantially with age. Like GH, androgens perform a wide range of beneficial functions throughout the body. In the liver, they decrease the production of sex hormone-binding globulin and other hormone-binding globulins. Androgens serve to stimulate the proliferation of bone cells in vitro, a function that becomes increasingly beneficial with age, as peak bone mass in men is in their mid-twenty's and linearly declines with age after that point. The hematologic and immunologic effects of androgens include the stimulation of the production of erythropoietin in the kidneys, which increases hemoglobin concentrations. A weak androgen known as Danazol is used to treat endometriosis in women due to its direct antiprogestational effects on the endometrium. Finally, testosterone treatment may help to decrease the symptoms of autoimmune disease. Though women have higher incidences of autoimmune disease than men, women also have greater humoral and cell-mediated immunity than men.

1. Testosterone

Testosterone has been shown to lower cholesterol and normalize the abnormal electrocardiograms of patients. Testosterone can also improve diabetic retinopathy as well as lower the insulin requirements of diabetic patients and decrease the percentage of body fat. Administration of testosterone to men has been reported to decrease risk factors for heart attack and low testosterone is also correlated with hypertension, obesity, and increased waist-to-hip ratio.

Research into "male menopause" or andropause shows that there is a drastic drop of serum levels of free testosterone of about 1.5% per year. While the total testosterone of a male does not drop drastically, the free testosterone, which is the biologically active part of the testosterone, does drop precipitously with aging. In fact, a significant drop of free testosterone can occur as early as the early 40s. FIG. 2 illustrates the decline of free testosterone over a male's lifetime. Studies have shown that men with high testosterone levels live longer, healthier lives and maintain sexual potency. Recent studies have also shown that testosterone has the ability to stop the spread of breast cancer in females. Additionally, for many years research has shown that testosterone has a protective effect against autoimmune diseases.

In the past, doctors were hesitant to supplement testosterone levels in healthy men for fear of increased risk of prostate cancer. Recent data suggests that testosterone is not the causal factor in the development of prostate cancer. One study examined three groups of age-matched men: One group was free of prostate cancer; one group had been diagnosed with benign prostate cancer and had undergone simple prostatectomy to remove it; and one group was diagnosed with prostate cancer. Total testosterone levels and free testosterone levels were measured. No significant differences were found in age-adjusted total testosterone or free testosterone at 0–5, 5–10, or 10–15 years before diagnosis. This data suggests that there are no measurable differences in testosterone levels among men who are destined to develop prostate cancer and those without the disease.

2. Estrogen/Progesterone

The female hormones, estrogen and progesterone, are known to drop drastically to very low levels after menopause. FIG. 3 shows the levels of estrogen and progesterone in a female and illustrates that those levels decrease after menopause. Several prestigious medical groups, including the American College of Physicians and the American College of Obstetricians and Gynecologists have released position papers saying post-menopausal women should seriously consider preventive estrogen/progesterone hormone replacement therapy for their benefit in reducing osteoporosis and heart disease, the major scourges of old age in women. Maintaining estrogen and progesterone levels has also been shown to improve a number of key risk factors for heart disease in post-menopausal women.

The benefits of estrogen/progesterone hormone replenishment therapy include prevention of osteoporosis and heart disease, prevention of vaginal dryness and thinning of the vaginal wall, relief from menopausal symptoms and hot flashes, and the possible benefit of reducing the onset of Alzheimer's disease, dementia, and cataracts. Studies have shown that when estrogen is replenished in conjunction with progesterone, the risks of uterine or breast cancer is nullified.

C. The Pineal Gland and Melatonin Hormone

Melatonin is another hormone that decreases substantially with advancing age. FIG. 4 presents a graph of nighttime melatonin levels produced throughout life and shows the gradual decline of these levels.

Melatonin is secreted by the pineal gland in the brain. Chemically, melatonin is a derivative of tryptophane. Melatonin is generating strong scientific interest as one of the body's most powerful regulators of the body's biological clock and immune system. It is known that the quantity of melatonin that is secreted declines with age, being highest in children from 1–3 years old and lowest in the elderly. This shift is believed to be an "age signal" to the cells. Pineal gland transplant studies in mice showed that when the pineal glands of young mice were transplanted to old mice, the old mice lived out the longer remaining life span of the young mice, and vice versa.

Melatonin enhances the immune system and has been found to have a powerful inhibitory effect on some cancer cells. Further, melatonin has been shown to amplify immune effects of interleukin-2 and to protect against chemotherapy-induced toxicity. In tissue cultures, melatonin has direct lethal action on melanoma cancer cells and estrogen-sensitive breast cancer cells. Melatonin has also been found to inhibit prostatic cancer cells from proliferation.

Also related to immunity is the research that has shown the dramatic effect of melatonin on the thymus gland. The thymus gland is important in the defense against infection. It appears that the thymus gland undergoes a transformation as we age: The thymus gland grows steadily large as we approach puberty, then begins to shrink until, in old age, it has virtually disappeared. As the thymus declines, so does our infection-fighting ability. Melatonin appears to protect this gland and improve its functioning as we grow older.

Studies have shown that melatonin is a more powerful antioxidant than vitamins E and C as acting as a "free-radical scavenger" and for protection against aging. Melatonin is also more efficient than vitamin E as a scavenger of the peroxyl radical, which contributes to massive lipid destruction in cell membranes. Melatonin also protects against a variety of degenerative and age-related neurological conditions of the brain, such as Parkinson's disease, Alzheimer's disease, schizophrenia, and depression. Finally, melatonin has also been shown to prevent cataracts.

Melatonin has by all evidence been shown to be completely harmless to the body. In other words, no matter how high the levels, melatonin apparently causes no side effects other than a natural drowsiness.

D. Dehydroepiandrosterone (DHEA)

The hormone DHEA is produced from cholesterol in the adrenal glands and serves a wide variety of functions, providing health and longevity benefits. It is a "mother" hormone that the body converts on demand into such hormones as estrogen, progesterone, testosterone, and androstenedione.

DHEA usually begins to appear in the bloodstream at the age of seven and peaks at about twenty-five years old. After that point, DHEA declines with advancing age. Around the ages of sixty to eighty an individual produces only 10–20% of the DHEA that was produced in the second decade of life. Males generally produce higher levels of DHEA than females until old-age brings the DHEA in both males and females to comparable levels. FIG. 5 presents a graph showing the production of DHEA and age and shows the decline of this production with age.

Studies have shown a direct relationship between blood levels of DHEA and the inhibition of many diseases, and its decline signals the onset of many age-related illnesses. DHEA levels in the blood can indicate the present and future status of a person with regards to cancer, immune function, cardiovascular disease, memory disorder, and aging itself.

E. Pregnenolone Hormone

Historically, pregnenolone has been known as the precursor to the DHEA hormone. It was thought for many decades to have played no additional biological role. However, recent research has found that pregnenolone has many independent and significant biological capacities and is considered a neural hormone with biological functions throughout the entire body, including the spinal cord and the brain.

Pregnenolone levels are similar in both males and females. Studies have shown that at birth the values are very high, at about 109 $\mu$g/dl of blood. During the first day of life levels may drop to 86 $\mu$g/dl of blood, and decrease to a mean value of 53 μg/dl during the first month, 11μg/dl between four and six months, and 3.7 μg/dl between seven and twelve months. At two years, pregnenolone levels are quite low, remaining so throughout the ninth year. This is followed by a progressive rise until adulthood, when adults are found to have pregnenolone levels that are three to four times higher than those found during the first decade of life. Brain concentrations of pregnenolone peak at around age 30 and later decrease to 5% of that value.

Pregnenolone is a steroid precursor produced in the human adrenal gland and in the human brain. Pregnenolone is produced in the desired amounts only if a person's body has adequate amounts of cholesterol, vitamin A, thyroid hormone, and enzymes. If these levels are insufficient, a low supply of pregnenolone will result.

In a healthy person, the conversion of cholesterol to pregnenolone occurs inside the mitochondria. Once produced, pregnenolone leaves the mitochondria and does not inhibit its own synthesis. In fact, both progesterone and pregnenolone stimulate their own synthesis. Therefore additional doses do not suppress the body's ability to synthesis these hormones. In the cell cytoplasm, enzymes convert pregnenolone into either progesterone or DHEA, depending on the type of cell and the present need. These are then the precursors for the more specialized steroid hormones, including cortisol, aldosterone, estrogen, and testosterone.

Of all steroidal hormones, pregnenolone has the greatest memory-enhancing effect, and can improve post-learning memory function at a dose 100 times lower than other memory-promoting steroids. This result has been observed in rats and mice, and such research has been documented extensively. Scientists found a positive correlation between the ability of rats to perform recognition tasks and the concentration of pregnenolone in the brain. Stated simply, animals that performed best had the highest pregnenolone levels. Researchers have also found that pregnenolone may help restore impaired memory. Their findings report that pregnenolone restores normal levels of memory hormones that decline during the aging process and at a rate several hundred times more potent than any memory enhancer previously tested.

Pregnenolone also appears to have the ability to repair enzyme activity. A Russian study demonstrated that adding pregnenolone to a mitochondrial suspension increased the activity of the enzyme that converts cholesterol into pregnenolone.

Scientists have also found that pregnenolone has anti-inflammatory effects. When it was administered immediately after a spinal cord injury, it reduced histopathological changes, spared tissue, and aided the restoration of motor function. Pregnenolone therapy is recommended for all diabetics past the age of 40 and is sometimes appropriate for younger patients. Pregnenolone was shown to rejuvenate the beta cells of the pancreas in diabetic animals and could be very helpful in humans as well.

Pregnenolone was used in the late 40's to treat rheumatoid arthritis but fell into disuse when cortisone was discovered. Pregnenolone has none of the side effects associated with cortisone.

F. Thymic Hormone and the Immune System

The thymus gland is the primary lymphatic tissue located in the thorax behind the sternum. The thymus gland is large at birth but atrophies completely by the second decade of life. The thymus gland's function is to nurture lymphocytes and it does so by secreting a hormone.

T-lymphocytes are designated as such because they are derived from or influenced by the thymus hormone. To become mature, all T-lymphocytes must reside in the thymus gland for a period of time. The cell in the thymus gland is called a thymocyte and acquires either CD4 or CD8 characteristics. The CD classification is given to further differentiate the types of T-lymphocytes. During the maturation period within the thymus gland, T-lymphocytes eventually become either CD4 cells or CD8 cells. Only those thymocytes expressing CD4 or CD8 characteristics are positively selected to emigrate, by way of the thymus gland, to the lymphatic system. This differentiation process results in mature lymphocytes that can recognize foreign bodies, viruses, or cancer cells in the context of major histocompatible complex hormones. Thus, CD4 cells are known as "helper" cells because they "help" the immune system by recognizing foreign substances on contact. CD8 cells are called T-suppresser/cytotoxic or "killer" cells. CD8 cells require histocompatible expression on target cells to be activated.

Studies have identified at least six types of thymic cells. The six types of cells produce interleukin-1 (IL-1), interleukin-4 (IL-4), interleukin-6 (IL-6), thymosin, thymopoietin, and thymulin. These hormones, secreted by the thymus gland, are found to have an effect on T-lymphocyte differentiation and activation. Of these thymic hormones, thymosin, thymulin, and thymopoietin in thymic humoral factor, may possibly reach the circulation and act on the lymphocytes and tissues at various sites in the human body.

Research has identified the dependence of the central nervous system's development on thymus gland function. Other studies have established an important interaction between the thymus gland and the development of the pituitary gland in the brain. The age-related deterioration of learning and memory abilities has also been linked to the atrophy of the thymus gland.

In addition to the central nervous system, the thymus gland may also affect functions of other endocrine tissues. For example, congenital absence of the thymus gland is associated with alterations of the pituitary gland, adrenal gland, thyroid, and ovaries. Antithyroid drugs that induce hypothyroidism also cause a marked atrophy of the thymus gland. T-4 is one type of thyroid hormone. When its levels were reduced following anti-thyroid medication treatment, the thymocyte population in the thymus gland was also reduced. Conversely, when T-3, a different type of thyroid hormone, was administered in mice, multifacilitated effects on thymus gland function were produced. Those effects included increased weight and cell population as well as enhanced thymocyte production. Within thirty days after surgery, removal of the pituitary gland resulted in a 50% reduction in both thymus gland weight and the concentration of thymus hormone known as thymosin.

Over the last twenty years, at least four separate and distinct thymus preparations have been isolated and analyzed for T-lymphocyte-regulating properties. Thymosin, thymulin, thymopoietin, and thymic humoral factor (THF) have all been utilized as thymic hormonal preparations for hormone replacement therapy.

Thymosin (TF) is a group of low molecular weight proteins extracted from bovine thymus. Thymosin has displayed potent stimulatory effects on T-lymphocyte-mediated immunity. Thymosin increased lymphocyte activity and enhanced IL-6 production in spleen cells. Thymosin had a stimulating effect on luteinizing hormone and gonadotropin releasing hormone, both pituitary hormones, in vivo studies of pituitary tissues. The release of another pituitary hormone known as prolactin, as well as human growth hormone and adrenal corticotropin (ACTH) are increased by in vitro thymosin studies. Luteinizing hormone was not increased by thymosin in vitro.

Thymulin is a protein extracted from porcine thymus tissue. It affects the differentiation of immature bone marrow cells and the function of T-lymphocytes. This thymic hormone stimulates CD-8 "killer" cell lymphocyte activity in the spleen cell cultures obtained from old, but not young, mice. The serum level of thymulin decreases with age, and it coincides with thymus atrophy. Thymulin requires zinc for full biological activity. patients who suffer from Crohn's disease or acute lymphobiastic leukemia are zinc deficient. They also have a reduction in thymulin activity. Young and old rats increased circulation thymulin levels in response to administration of growth hormone and thyroid hormone injections.

THF is an extract of calf thymus. Interleukin-2 (IL-2) is a protein manufactured by lymphocytes. It was enhanced by the influence of THF in spleen cell cultures. Peripheral blood obtained from patients with chronic hepatitis B and viral infections responded to THF with increased production of IL-2. This suggests a possible antiviral role for this thymic hormone.

Thymopoietin is a protein isolated from bovine thymus gland. Thymopoietin enhances T-lymphocyte differentiation and the effect of function on mature T-lymphocytes.

Various studies teach that the thymus gland and thymic hormones contribute to human immunity, the neuroendocrine system, the reproductive system, and the development of the central nervous system. Additionally, alteration in the status of the thyroid, adrenal, and pituitary glands, as well as the kidney, have affected the structure and function of the thymus gland. Finally, results indicate that the presence of thymic hormone in circulation can have an affect on a variety of other organ systems.

G. Human Biological Age

Aging is a syndrome controlled by the inborn processes of progressive tissue injury (formation of free radicals from oxidation), a neuroendocrine clock (with declining levels of various hormones), and declining DNA repair capacity. To date, research has ignored efforts to forestall or reverse the aging syndrome by controlling these processes, particularly the neuroendocrine clock.

The tests for biological aging fall into basically two levels. One, a functional level that deals with the activities of a person, and two, a cellular or molecular level (changes in the cells and molecules of the body). The functional level biological aging tests are: Forced vital capacity, muscle function (such as hand grip strength), cardiac function, aerobic capacity, and renal (kidney) function. At the cellular level, the tests are: Bone loss, fingernail growth rate, change in percentage of body lean muscle, declining levels in various hormones, sensory and neurologic deficits, and decrease in immune function. The following paragraphs describe these functional and cellular levels.

Forced vital capacity changing with age is well demonstrated. Excess mortality at low forced vital capacity was noted in elderly as well as in the young, in most sexes, and in non-smokers as well as smokers. The reason for the decreased forced vital capacity could be due to the loss of muscle power or a stiffer, less compliant chest wall or diaphragm.

Aging is also associated with decreased muscle function/mass. This causes a decrease in hand grip strength and decreased physical endurance and physical capacity. Hand grip strength can be simply measured by dynamometer and muscle functions of different extremities can be measured by isokinetic machines. Age is also associated with an increase in percentage of body fat. This change can be measured by skin calipers, skin impedance measurements, and the water immersion method.

It has been known for many years that aging is associated with decreasing resting cardiac output. The cardiac output and age are inversely related. Cardiac function can be determined by cardiac hemodynamic studies conducted in a cardiologist's office. Aerobic capacity also declines with age. Aerobic capacity may also be simply measured in a doctor's office.

Progressive decline in renal function is also associated with age and begins essentially in the middle of the fourth decade. This can be documented by kidney creatinine clearance (filtration) tests.

Bone loss is a significant problem leading to skeletal collapse and fractures, and is the leading cause of disability in elderly women. Bone loss can be documented by radio isotope bone scan, which is easily performed in most hospitals radiology departments.

Studies have shown that the rate of fingernail growth, measured over one year, can give quantifiable information when correlated with age. Linear nail growth decreases 50% over the life span of the human. Changes in fingernail growth rate can be measured by marking the fingernail.

Decrease in neurological functions is also noticed with increased age such as hearing functions, visual functions, reaction time, and memory. These can be measured individually by a physician in an office setting.

The skin also undergoes changes with age. This can be measured by skin biopsy or skin turgor test. Skin turgor is measured by pulling up the skin on the back of the hand and observing the time it takes for the skin to return to its natural position.

There are many hormones that decline with age. Some decline in a linear fashion and others do not. Of the various hormones, DHEA and melatonin decline in the most linear fashion beginning in the third decade of life. Therefore, the DHEA hormone (produced by the adrenals) and the melatonin hormone (produced by the pineal gland) are the most accurate in predicting biological age. Other hormones that decline with age are human growth hormone, the sex hormones such as testosterone, estrogen, and progesterone, and sometimes the thyroid hormones.

Immune responses decrease in the elderly such that skin allergy test responses are reduced significantly in this population. This can be tested with tuberculin or tetanus skin tests which measure the extent of and duration (reaction or lack of it) after two days. Human cytokine production also declines with age and the interleukin-2 decreases with age, whereas interleukin-3, -4, and -10 increase with age. The B-lymphocyte cells, monocytes, and macrophages remain unchanged with age; however, the number of T cell lymphocytes and natural killing cells (NK cells) also decrease with age, particularly the CD3, CD4, and CD8 cells. Not only the number, but the response of T cells also decreases with age. There is a marked age-related decline in human IgG antibodies and a less marked decline in IgM antibodies beginning at age 60. This explains one reason why people over 60 are more susceptible to infection.

G. Hormone Therapy and Aging

As noted above, many hormones decline with age. Certain hormone therapies, for example HGH therapy, have been studied for its effect on aging. HGH therapy has been experimentally used to study its ability to increase muscle mass and strength in elderly subjects. HGH therapy has also been used to treat diseases of the central nervous system such as Alzheimer's disease, Parkinson's disease, and senile dementia. Thus far, treatment with growth hormone and other hormone therapies in studying the effects of age and treating age-related illnesses has focused on pharmacological levels of treatment. The studies have not sought to mimic the human body's natural production of growth hormone. Similarly, treatments have been administered using other hormones that decrease with age, but again these studies focus on pharmacological levels of treatment. The studies and treatment have not sought to maintain peak physiological levels of the supplemented hormones.

SUMMARY OF THE INVENTION

The invention relates to a hormone replenishment method particularly useful in maintaining the body's neuroendocrine clock at optimal levels and combating conditions (e.g., illness, disease, and minimized independence) associated with advancing age. The method includes determining that the level of human growth hormone and at least two other supplemental hormones are below pre-determined physiological levels for an adult human. Once it has been established that the level of human growth hormone and at least two of certain supplemental hormones are below predetermined physiological levels, the method includes establishing a regimen for the replenishment of the level of the deficient hormones to optimal or pre-determined physiological levels. The supplemental hormones include the sex hormones, namely testosterone, progesterone, and estrogen, the pineal hormone, melatonin, the adrenal hormones, namely DHEA and pregnenolone, the thyroid hormone, and the thymus hormone. The invention also relates to a method of increasing life expectancy by determining the level of human growth hormone and at least two of the supplemental hormones and establishing a regimen for the maintenance of the level of human growth hormone and supplemental hormones at optimal or pre-determined physiological levels.

BRIEF DESCRIPTION OF THE DRAWINGS

FIG. 10 presents the effects of HGH administered to patients according to the invention.

DETAILED DESCRIPTION OF THE INVENTION

The invention relates to a hormone replenishment method of increasing life expectancy. The method includes determining that the level of human growth hormone and at least two supplemental hormones are below optimal or pre-determined physiological levels for an adult human, and establishing a regimen for the replenishment of the level of the deficient hormones to optimal or pre-determined physiological levels. The supplemental hormones include the sex hormones, namely testosterone, progesterone, and estrogen, the melatonin hormone, the adrenal hormones, namely DHEA and pregnenolone, the thyroid hormone, and the thymus hormone.

Optimal or pre-determined physiological levels for the hormones included in the replenishment and to increase life expectancy are set forth in Table I.

Figure 1:
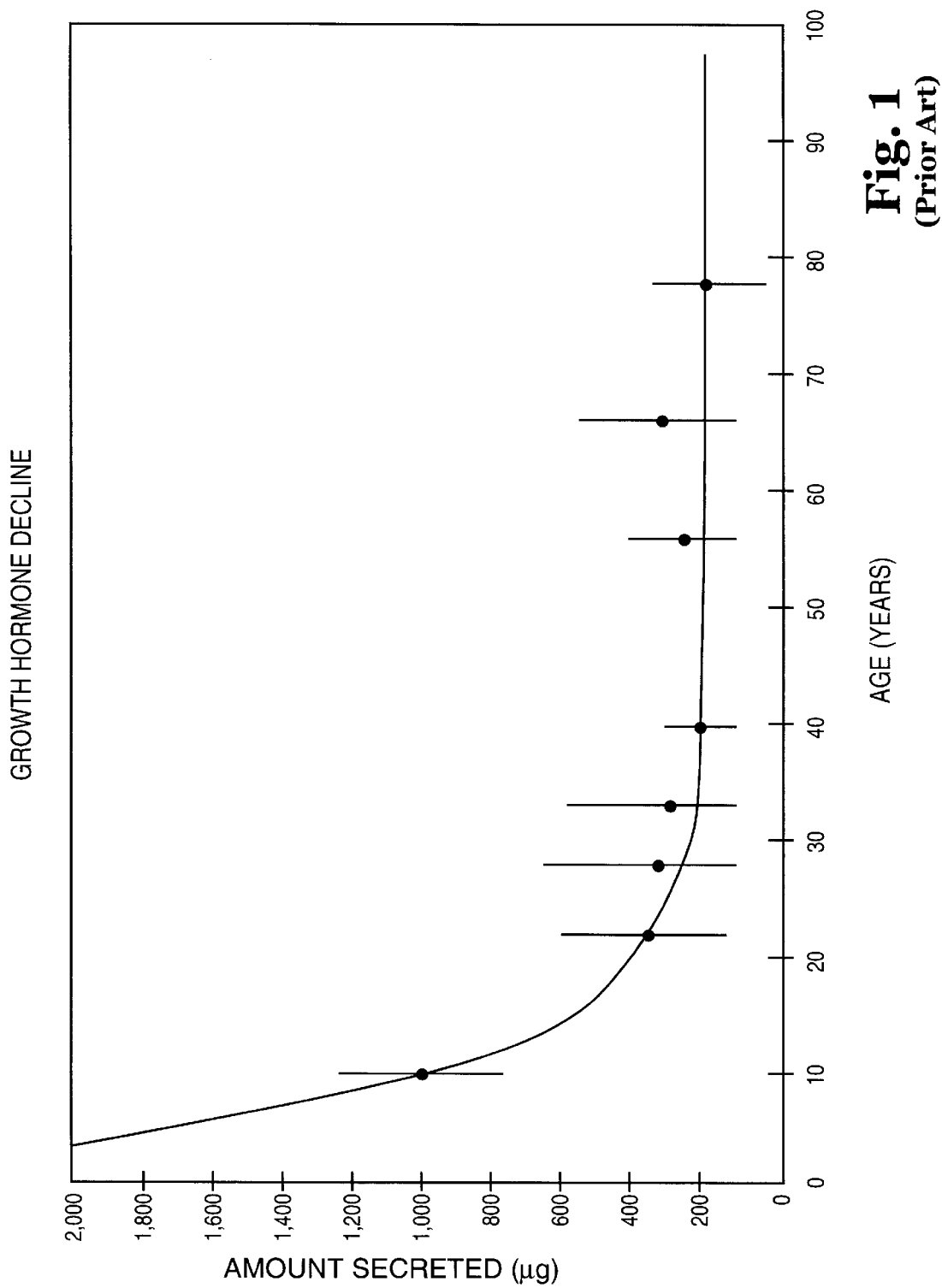
FIG. 1 illustrates the growth hormone decline in advancing years.
Figure 2:
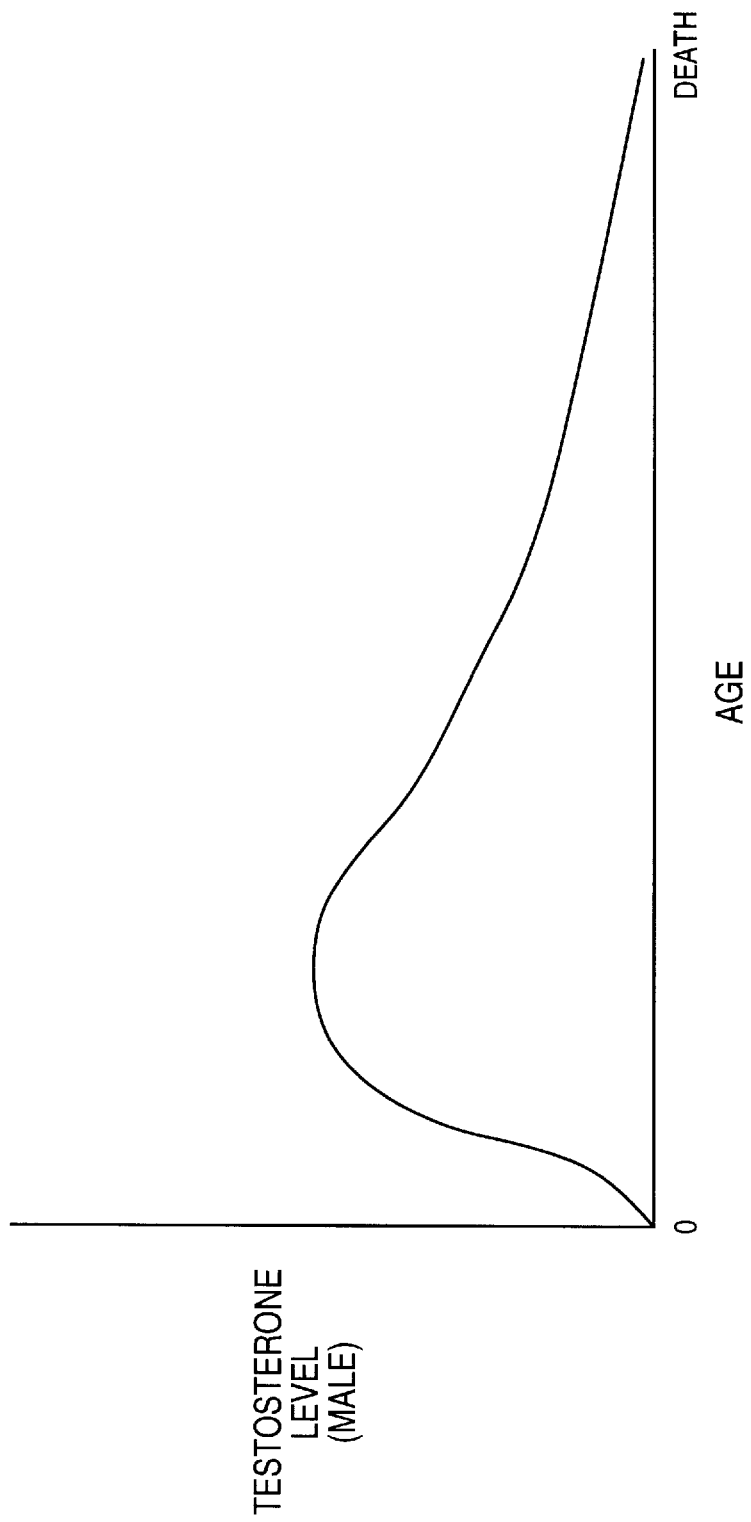
FIG. 2 illustrates the free testosterone levels in males throughout life.
Figure 3:
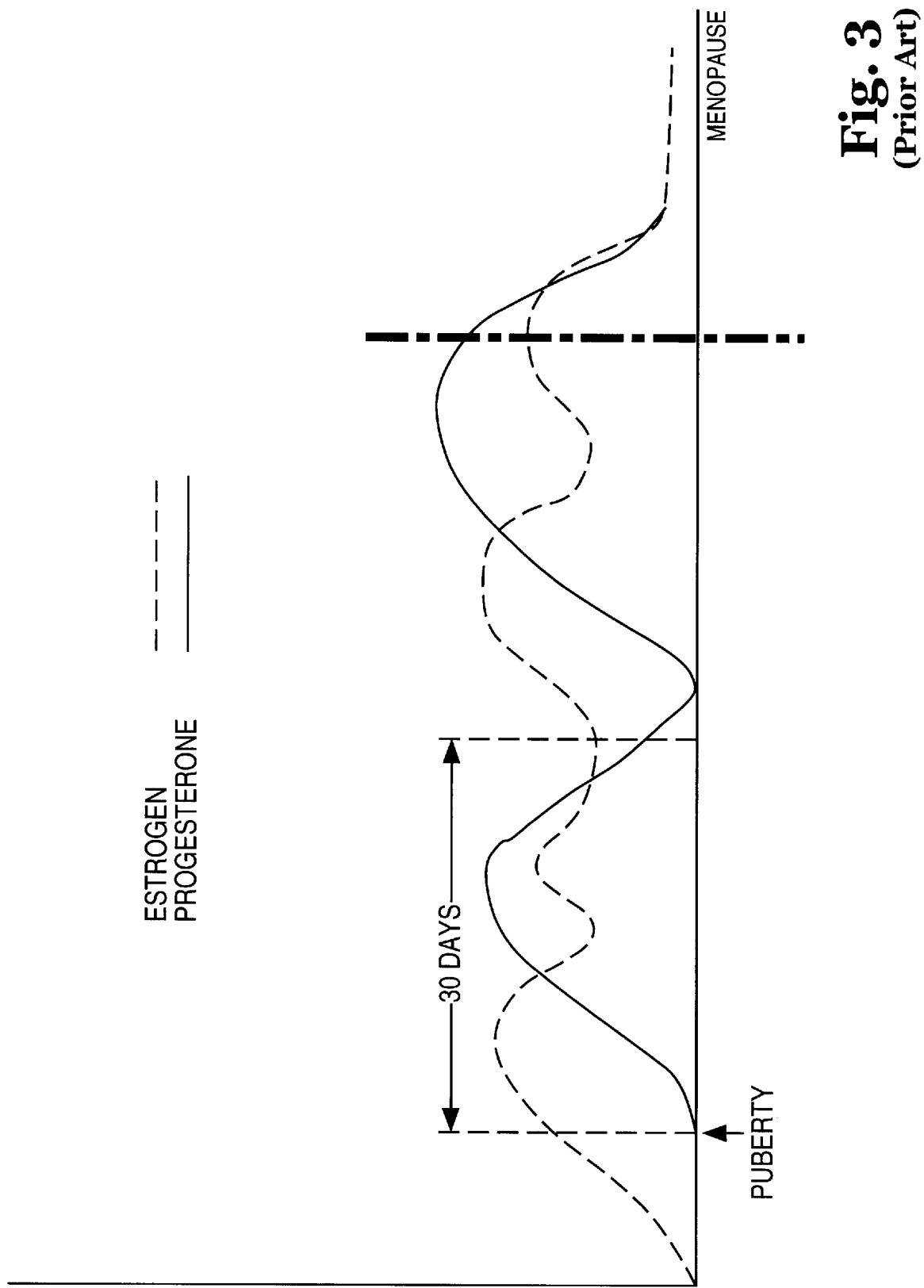
FIG. 3 illustrates the levels of estrogen and progesterone in females before and after menopause.
Figure 4:
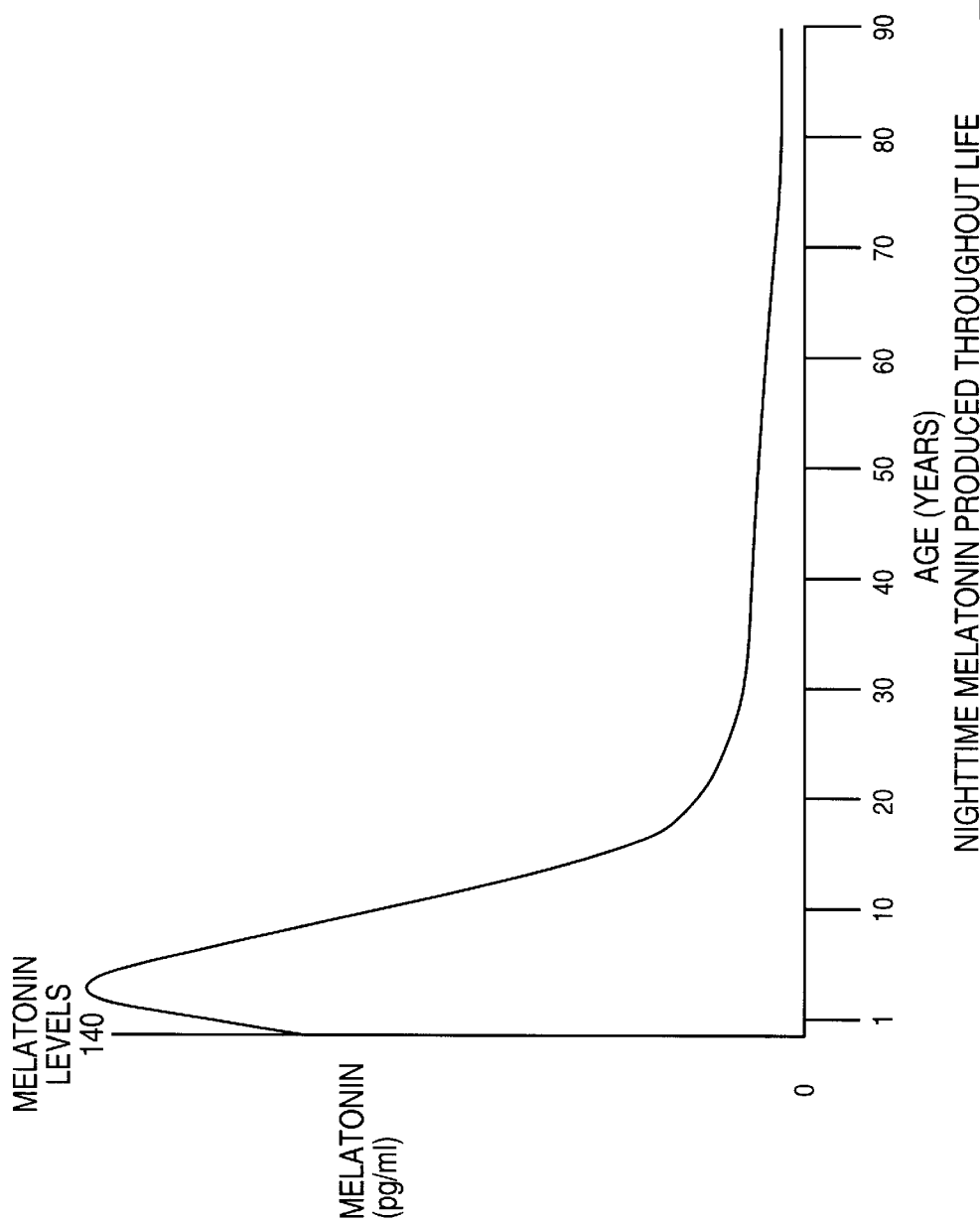
FIG. 4 illustrates the melatonin levels produced throughout life.
Figure 5:
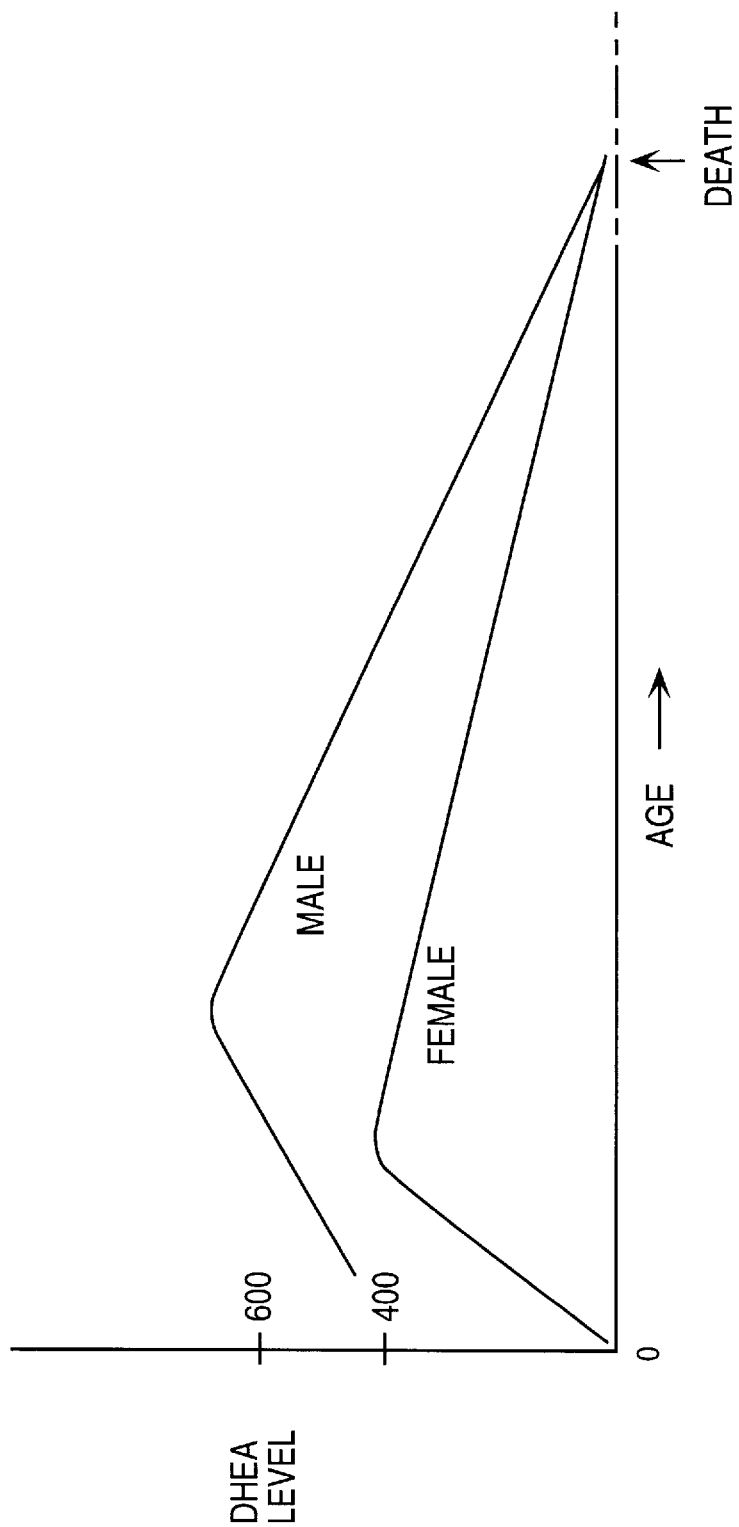
FIG. 5 illustrates the DHEA levels for males and females over a life span.
Figure 6:
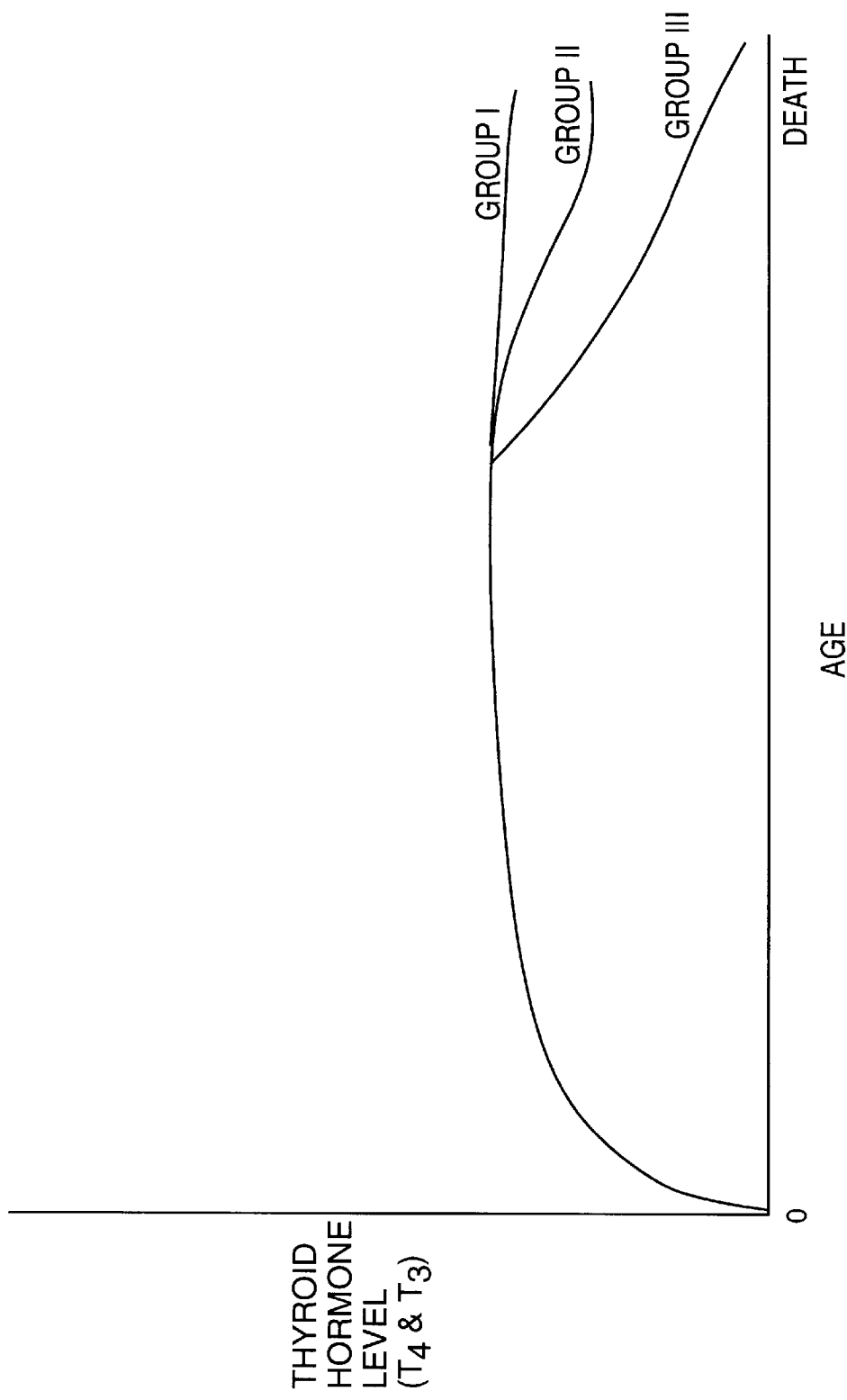
FIG. 6 illustrates the thyroid hormone levels versus age.
Figure 7:
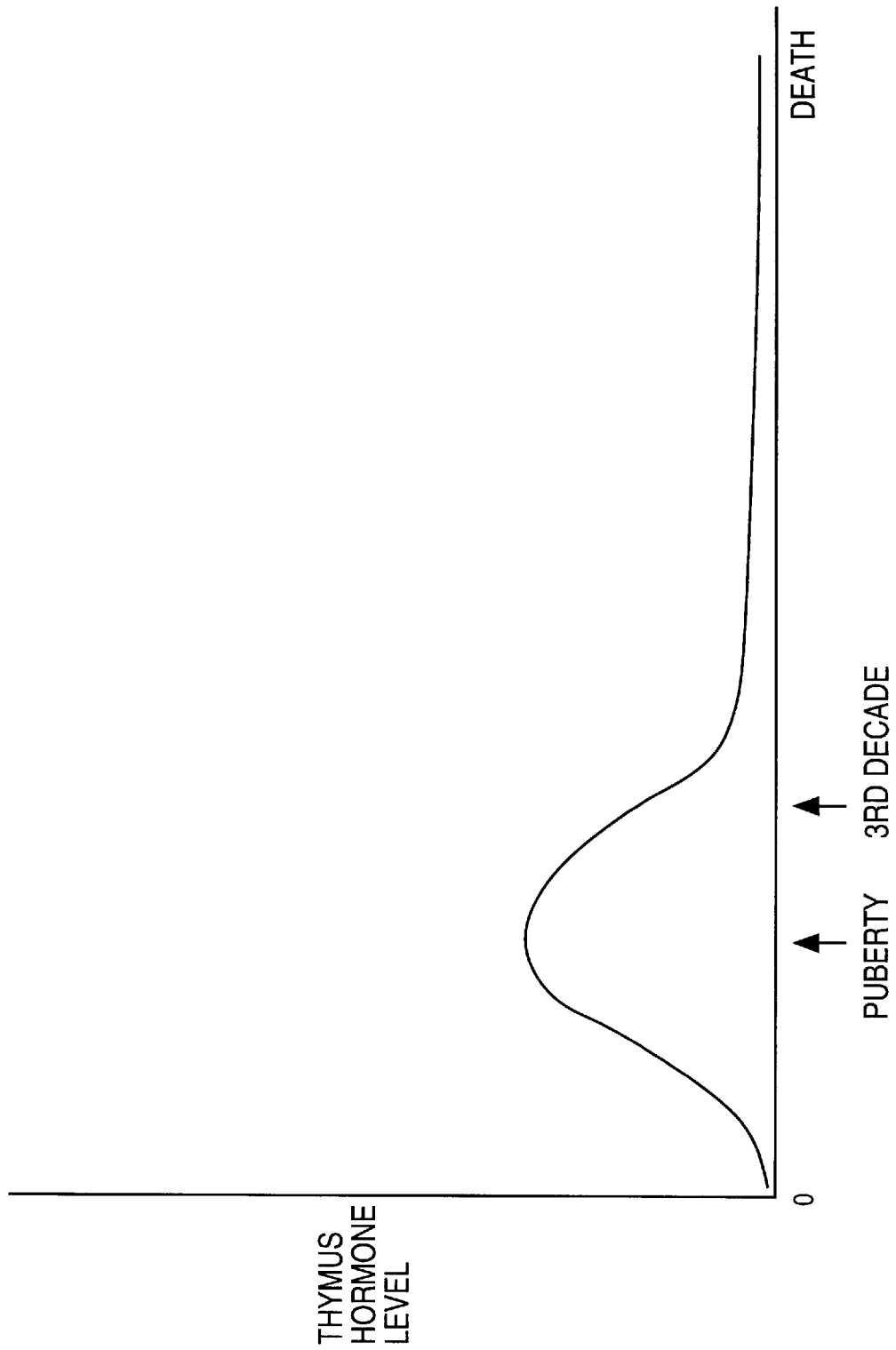
FIG. 7 illustrates the thymus hormone levels versus age.
Figure 8:
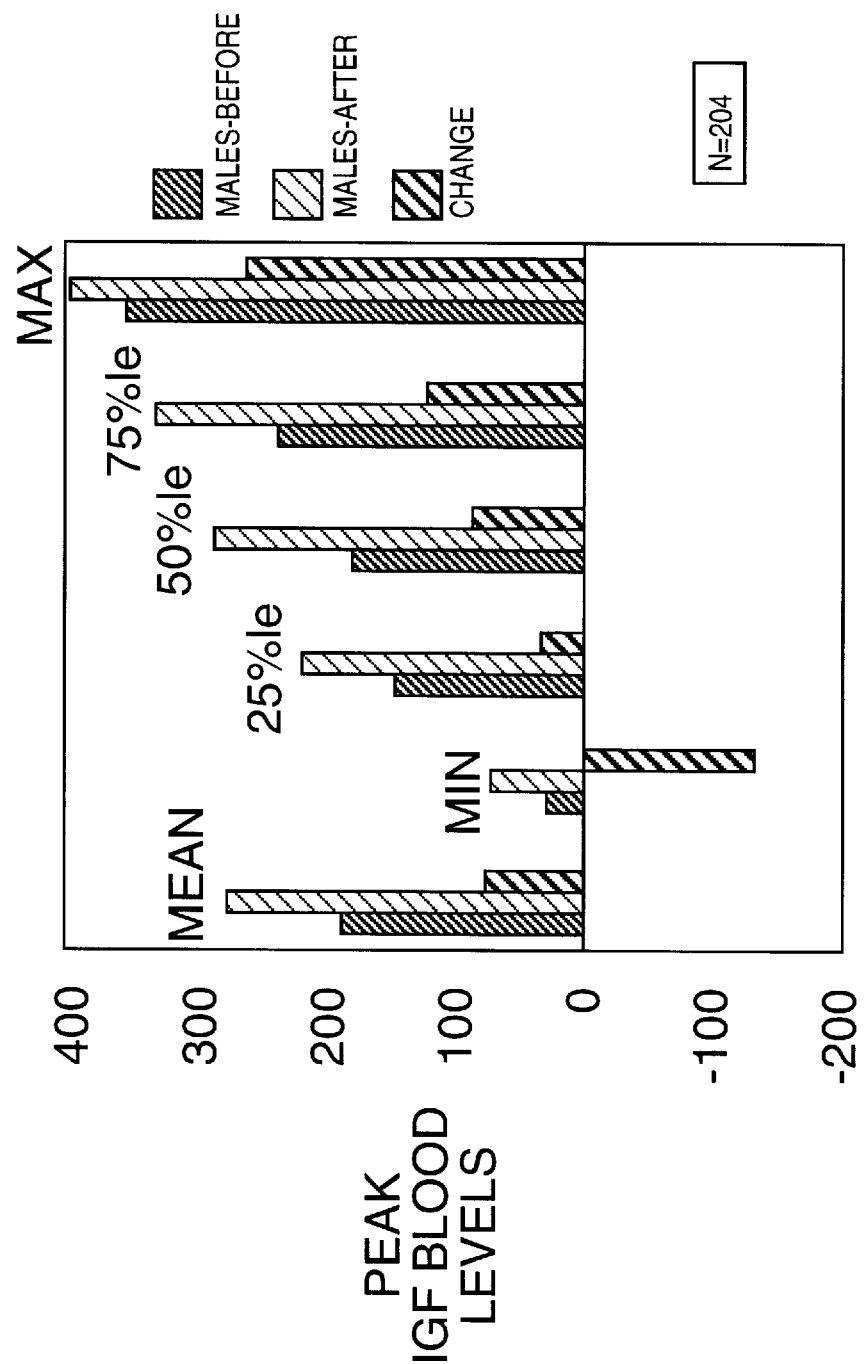
FIG. 8 presents the peak IGF-I levels in males before and after administration of IGF-I.
Figure 9:
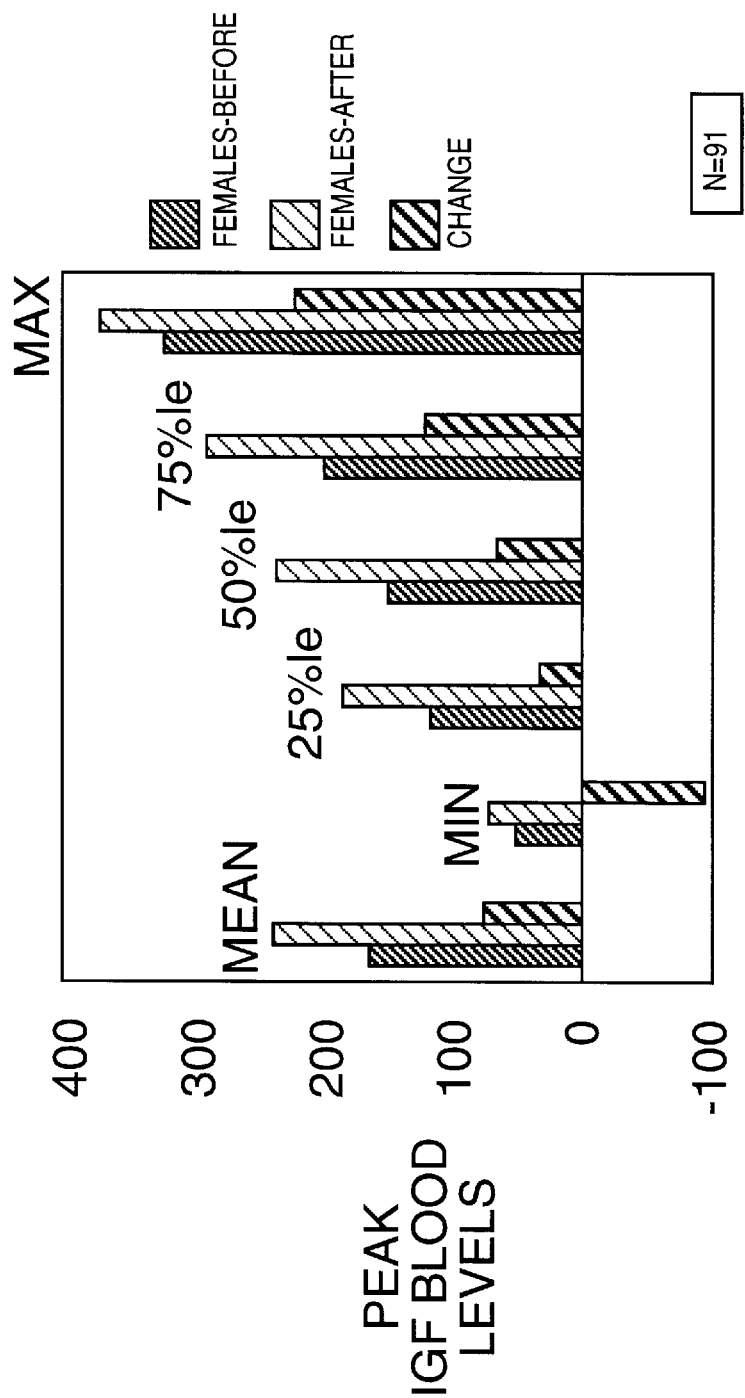
FIG. 9 presents the peak IGF-I levels in females before and after administration of IGF-I.

Table I shows that the HGH is measured by the level of IGF-I. Serum levels of HGH are difficult to measure. IGF-I is directly dependent upon the secretion of HGH by the pituitary gland, so therefore there is a direct linkage between increased secretion of HGH and increased production of IGF-I. Table II presents the effects of the low dose at high frequency human growth hormone administration (low dose-high frequency) contemplated by the invention on IGF-I (somatomedin C) blood levels. FIGS. 8 and 9 present the peak IGF-I levels in males and females, respectively, before and after administration of IGF-I. FIGS. 8 and 9 show mean, minimum and maximum, and 25, 50, and 75 percentile for 204 males and 91 females, respectively. Table III shows the data presented in FIG. 8. Table IV shows the data presented in FIG. 9.

TABLE I

| HORMONE | METHOD OF ADMINISTRATION | TARGET LEVEL (μg/ml blood) |
|---|---|---|
| HGH | injection | IGF-I = 350 |
| free testosterone | gel | female = 3 male = 40 |
| progesterone | capsule | 10–25 |
| estrogen | capsule | 100–200 |
| melatonin | capsule | 18–69 (at 3:00 am) |
| DHEA | capsule | female = 400 male = 600 |
| thyroid | tablet | T3 = 150–180 |
| pregnenolone | capsule | 100–200 |
| thymus hormone | tablet | N/A |

TABLE II

Effects of Human Growth Hormone Administration (low dose-high frequency) on Somatomedin C Blood Levels Somatomedin C. Blood Levels (ng/ml)

|  | Before hGH | After hGH | Increase |
|---|---|---|---|
| Mean | 238.8 | 384.5 | 61.0% |
| STDEV | 62.3 | 50.8 |  |
| SEM | 9.1 | 7.4 |  |
| No. Patients | 47.0 | 47.0 |  |
| MAX | 366.0 | 574.0 |  |
| MIN | 132.0 | 301.0 |  |

P < 0001

TABLE III

Males

| PEAK | IFG SAMPLE SIZE | MALES BEFORE MEAN | MALES AFTER MEAN | MALES CHANGE MEAN | MALES DAYS MEAN |
|---|---|---|---|---|---|
| BEFORE | 204 | 192.3 | 266.7 | 74.4 | 118.5 |
| AFTER | 204 | MEDIAN | MEDIAN | MEDIAN | MEDIAN |
|  |  | 183 | 272.5 | 75.5 | 82 |
|  |  | STDEV | STDEV | STDEV | STDEV |
|  |  | 61.7 | 75.1 | 73.2 | 110.3 |
|  |  | MIN | MIN | MIN | MIN |
|  |  | 21 | 63 | −135 | 6 |
|  |  | 25% ile | 25% ile | 25% ile | 25% ile |
|  |  | 147 | 217 | 24 | 40 |
|  |  | 50% ile | 50% ile | 50% ile | 50% ile |
|  |  | 183 | 273 | 76 | 82 |
|  |  | 75% ile | 75% ile | 75% ile | 75% ile |
|  |  | 231 | 325 | 125 | 146 |
|  |  | MAX | MAX | MAX | MAX |
|  |  | 361 | 396 | 258 | 639 |

TABLE IV

Females

| PEAK | IFG LEVELS SAMPLE SIZE | FE-MALES BEFORE MEAN | FE-MALES AFTER MEAN | FE-MALES CHANGE MEAN | FE-MALES DAYS MEAN |
|---|---|---|---|---|---|
| BEFORE | 91 | 162.2 | 236.3 | 74.0 | 133.4 |
| AFTER | 91 | MEDIAN | MEDIAN | MEDIAN | MEDIAN |
|  |  | 154 | 240 | 72 | 101 |
|  |  | STDEV | STDEV | STDEV | STDEV |
|  |  | 61.5 | 75.1 | 73.6 | 113.8 |
|  |  | SEM | SEM | SEM | SEM |
|  |  | 6.4 | 5.9 | 4.8 | 13.2 |
|  |  | MIN | MIN | MIN | MIN |
|  |  | 41 | 52 | −93 | 26 |
|  |  | 25% ile | 25% ile | 25% ile | 25% ile |
|  |  | 111 | 177 | 26 | 49 |
|  |  | 50% ile | 50% ile | 50% ile | 50% ile |
|  |  | 164 | 240 | 72 | 101 |
|  |  | 75% ile | 75% ile | 75% ile | 75% ile |
|  |  | 205 | 294 | 128 | 173 |
|  |  | MAX | MAX | MAX | MAX |
|  |  | 311 | 378 | 231 | 534 |

The method of determining the level of the select group of hormones may be accomplished by a simple blood test. A patients' blood is evaluated for the hormone levels of the select group of hormones and those levels are compared to the optimal or pre-determined physiological levels set forth in Table I. Based on the comparison of a patient's hormone levels with the optimal or pre-determined physiological levels, a regimen is established for the patient for the replenishment of the level of deficient hormones to optimal physiological levels. It is further contemplated, that after the initial evaluation and the establishment of the regimen, a patient is monitored every 30 days, by a similar blood test, until the patient attains the optimal or pre-determined physiological level, and the dosages of hormone supplementation are adjusted accordingly. Once the target levels are established, the regimen directs that the patient continue to follow the established dosage of supplemental hormones indefinitely to maintain the optimal or pre-determined physiological levels. Periodic blood tests are subsequently administered to assure that the optimal or pre-determined physiological levels are maintained.

The optimal or pre-determined physiological level of HGH and the supplemental hormones are set forth in Table I. These levels recognize the importance of each hormone to the body and are based on studies that indicate the period of life when the individual hormones are at their peak in the human body—generally in the second and third decade of human life.

The method of the invention also contemplates that the HGH is administered in keeping with the way the pituitary secretes HGH naturally. The low dose-high frequency method mimics the pituitary gland. The pituitary secretes HGH 24 hours a day, with the peaks during the first two hours of sleep. The method contemplates that the patients take lower doses more frequently to try to mimic the natural rhythm of the body as much as possible. The invention contemplates that the patients take HGH injections at least twice daily. A preferred regimen calls for subcutaneous injections of doses less than 0.5 mg per day (approximately 1–3 I.U.), administered twice daily. Typical doses for this regimen range from 4 units per week to 8 units per week.

Because the invention contemplates that human growth hormone is administered in lower doses that mimic the natural rhythm of the body, the invention contemplates that the patient experiences none of the adverse side effects reported in earlier studies when higher pharmacological doses were given to patients more intermittently, e.g., 3 days per week.

Candidates for androgen-replacement therapy are those individuals with documented testosterone deficiency, generally men. Among these candidates, it is important to note the difference between primary and secondary hypogonadism before therapy commences. Primary hypogonadism entails an inability to synthesize normal quantities of androgens by the testes. Only exogenous hormone replacement stimulates and maintains androgen-dependent processes in such patients. Fertility cannot be induced by hormonal therapy in patients with primary hypogonadism. Patients with secondary hypogonadism do have the potential to be fertile, and can stimulate and maintain androgen-dependent processes through exogenous androgen treatment. Further, gonadotropin treatment can often stimulate spermatogenesis in such patients. However, patients with hypogonadism cannot expect to attain or regain fertility during androgen treatment. The safest choices of treatment of hypogonadism is with natural testosterone, as it does not have toxic side effects on the liver. An intramuscular regimen can sometimes cause oscillations in serum concentrations that can cause changes to physical functioning or behavior. Patients with prosatitic hypertrophy should initially receive a lower dose. Rarely does this treatment result in enlargement of the prostate or obstruction of the bladder.

Although testosterone replacement is essential, one must treat it with caution, as dihydrotestosterone (a metabolite of testosterone) accelerates prostatic cancer growth. Therefore, before a male patient is placed on testosterone, his physician should obtain a prostate specific antigen test for the presence of prostate cancer. Should the patient have prostate cancer, then testosterone replacement therapy is contraindicated. Other than this, physiologic doses of testosterone replacement have absolutely no adverse side effects.

Testosterone replacement therapy in the form of pellets of crystals remains the most effective and convenient form of treatment with synthetic testosterone. However, the best method of initiating testosterone replacement currently is via the transdermal method using natural testosterone rather than synthetic testosterone. Synthetic testosterone has been shown to cause hepatoxicity. Natural testosterone does not cause hepatoxicity. Natural testosterone is delivered either in a gel form or by a patch applied to the skin and released into the body gradually. The optimal or pre-determined physiological level goal in testosterone replacement therapy in men is to maintain a total testosterone level at about 900–1200 µg/ml and a free testosterone level of about 30–40 µg/ml throughout one's lifetime. In women, the levels of testosterone to maintain are much less, specifically women should maintain a free testosterone level of about 3 µg/ml.

Possible side effects which can occur during testosterone replacement include some weight gain due to accumulation of lean body mass and fluid retention; sleep apnea, which can occasionally develop or worsen during therapy, and among patients taking supraphysiologic doses of androgens, decrease testicular size, azoospermia, and acne.

As noted above, candidates for supplemental estrogen or progesterone should replenish these hormones concurrently to avoid the risk of side effects. These hormones may be taken in capsule form. The optimal or pre-determined target physiological level of progesterone is 10–25 µg/ml blood, and of estrogen is 100–200 µg/ml blood.

The optimal or pre-determined target physiological level of melatonin is 18–69 µg/ml determined by the average level of melatonin produced by a healthy young adult (i.e., 20–25 years). Further, melatonin supplementation has been shown to be completely harmless to the body and cause no side effects.

As noted above, the amount of DHEA peaks in the bloodstream of an individual at about 25 years of age. It is this physiological level that is the goal of the DHEA replenishment therapy. The optimal or pre-determined physiological level of DHEA in a female is 400 µg/ml blood and in a male is 600 µg/ml blood.

The serum level of pregnenolone for normal adults ranges between 50 to 350 µg/ml of blood. If a person's level is low and falls outside of this range, replacement is recommended. Depending on the degree to which a patient may be deficient, the dose is approximately 100–200 milligrams ("mg") each day. The older or less healthy a person is, the more likely he or she will feel a dramatic effect from pregnenolone. A blood test is required to determine each individual's need for pregnenolone replacement, and to assess the proper dosage for therapy.

Laboratory results indicate that the presence of thymic hormone in circulation can have an effect on a variety of other organ systems. All four thymic preparations (i.e., thymosin, thymulin, THF, and thymopoietin) are commercially available. Such a replacement therapy is totally harmless. The Food and Drug Administration has not regulated thymic hormones because they are not yet considered drugs or pharmaceuticals. Thymus hormone is in the same status and classification as DHEA and melatonin hormones which are also available over the counter.

By maintaining the optimal or pre-determined physiological levels of human growth hormone and the supplemental hormones described above, the treatment is effective at combating conditions associated with aging. FIG. 10 presents the effects of human growth hormone administered as contemplated by the invention, i.e., low does-high frequency. FIG. 10 shows the percent improvement in many of the functional and cellular levels associated with tests for aging. FIG. 10 shows improvement in the functional level biological aging tests of muscle function, cardiac function, aerobic capacity, and renal function. FIG. 10 also shows improvement of the cellular level biological aging tests including sensory and neurological capacity and immune function. Thus, FIG. 10 illustrates that the functional and cellular effects of aging restore vitality and health. By replacing hormones, the invention takes away one of the mechanisms of aging. The invention extends life expectancy, by maintaining the neuroendocrine functions at an optimal level, in essence, fooling the neuroendocrine clock.

Figure 11:
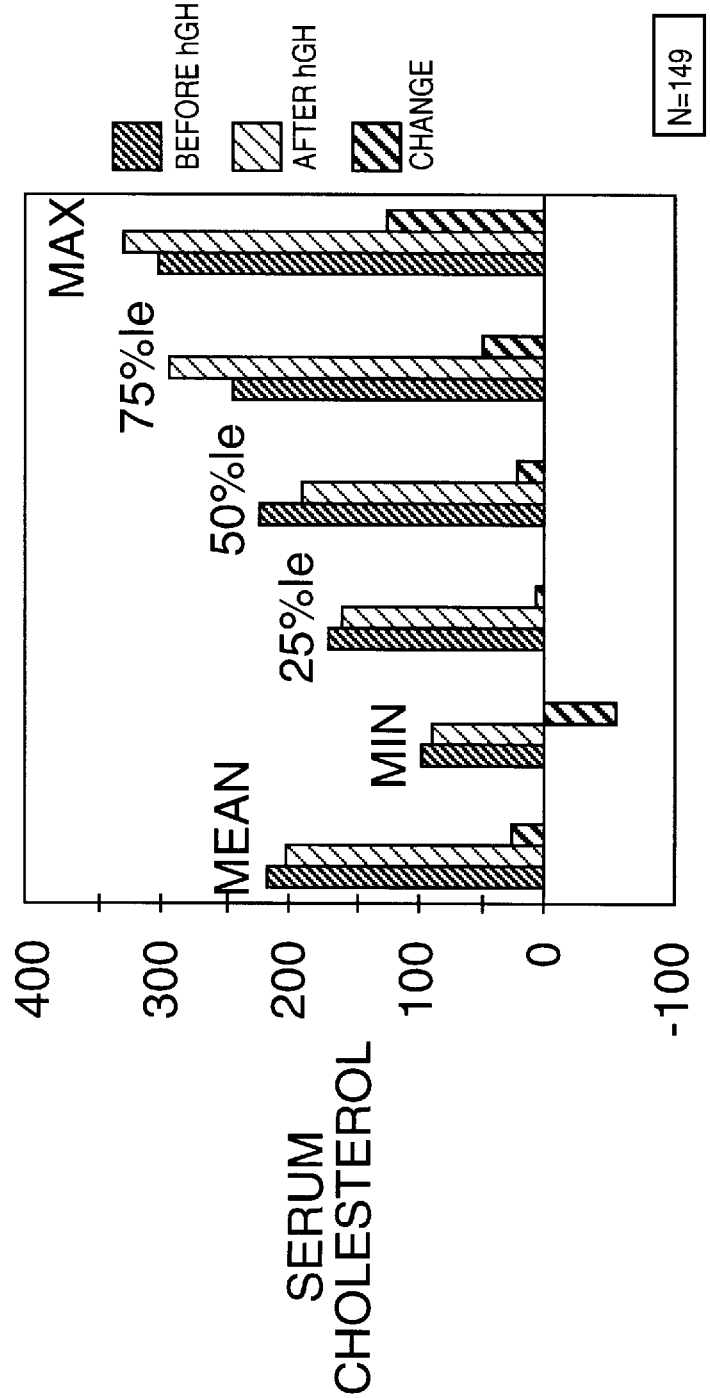
FIG. 11 presents the effect of hormone replacement therapy on cholesterol levels in males.
Figure 12:
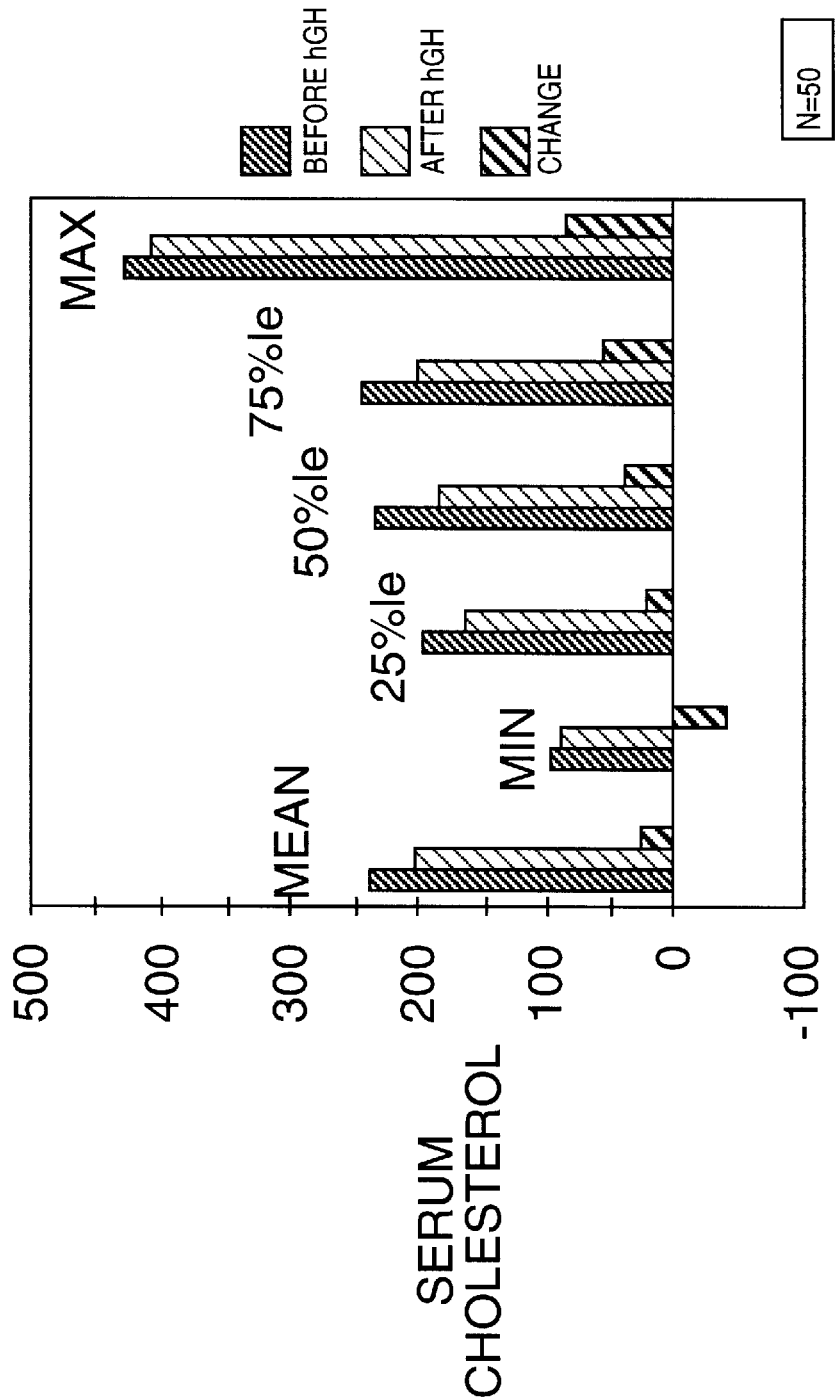
FIG. 12 presents the effect of hormone replacement therapy on cholesterol levels in females.

FIGS. 11 and 12 present the effect of hormone replacement therapy on cholesterol levels in males and females, respectively. FIG. 11 and 12 show that cholesterol levels decreased on average in both males (149 studied) and females (50 studied), respectively, after HGH administration. FIGS. 11 and 12 show mean, minimum and maximum and 25, 50, and 75 percentile values for 149 males and 50 females, respectively.

Figure 13:
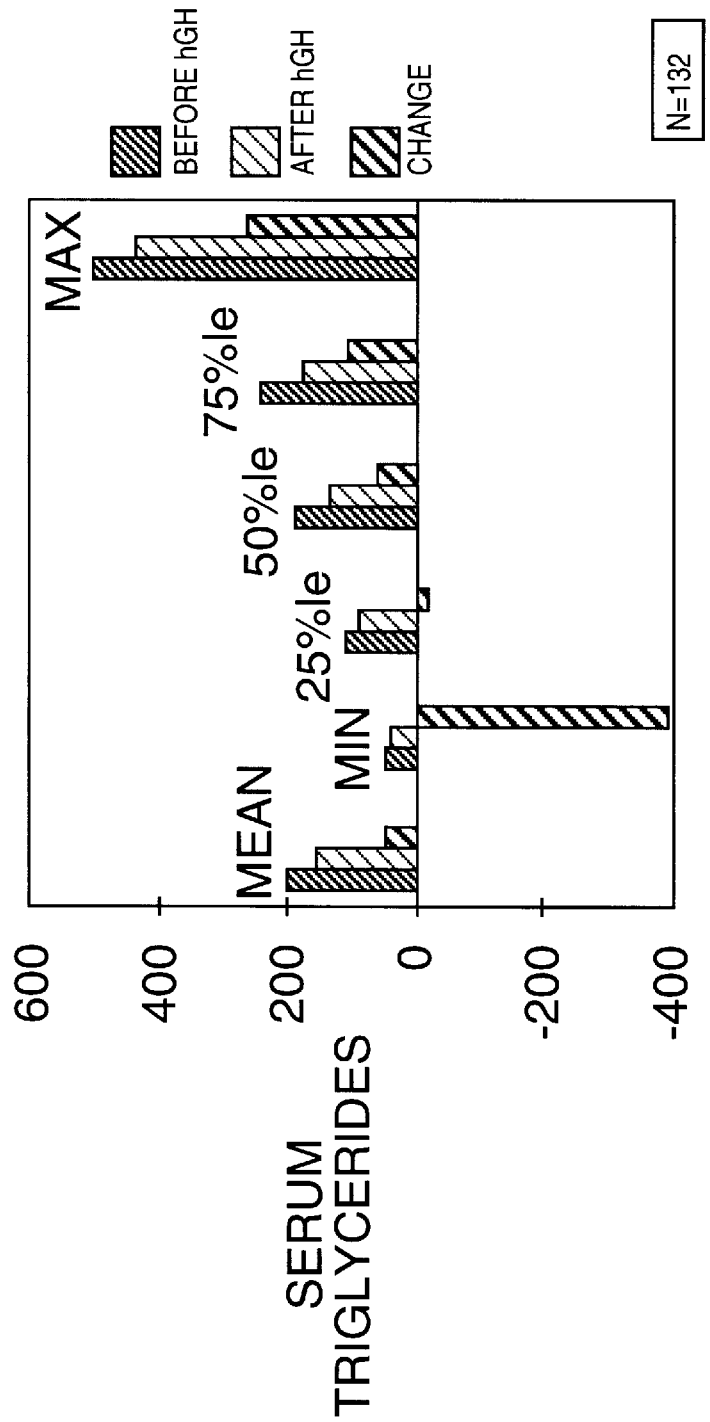
FIG. 13 presents the effect of hormone replacement therapy on triglyceride levels in males.

FIG. 13 presents the effect of hormone replacement therapy on triglyceride levels decreased on average after HGH administration. FIG. 13 shows mean, maximum and minimum, and 25, 50, and 75 percentile values.

Not only are the effects of optimal or pre-determined levels of human growth hormone administered according to the invention in a low dose-high frequency method beneficial to the reduction of the effects of aging, but maintaining the other supplemental hormones at optimal or pre-determined levels further minimizes the effects of biological age. For example, as stated above, a proper amount of testosterone eliminates andropause and decreases the risk for heart attack; estrogen/progesterone hormone replenishment relieves menopausal symptoms and hot flashes and possibly reduces the onset of Alzheimer's disease, dementia, and cataracts; optimal melatonin, DHEA, thyroid and thymus hormone levels enhance the immune system and inhibit many age-related diseases; and pregnenolone restores normal levels of memory hormones that decline during the aging process. In summary, optimal or pre-determined levels of human growth hormone and the supplemental hormones nullify the effects of biological aging. Accordingly, the invention contemplates an increased life expectancy by maintaining the optimal or pre-determined physiological levels of the prescribed hormones.

The results of a large clinical trial, i.e., greater than 1,000 patients, concluded that the high frequency/low dose method of administering HGH and the supplemental hormones increased IGF-I to youthful levels within 1–2 months. The most outstanding results saw improvements in muscle strength, exercise endurance, and loss of body fat. There was also significant improvements in skin, healing capacity, sexual drive and performance, energy level, emotion/attitude, and memory. In general, these improvements occurred within 1–3 and continued to increase over 6 months.

The following examples present blood measurements and physiological treatments prescribed for specific patients to bring those patients hormone levels to optimal or pre-determined physiological levels.

| Patient 1 (Female, Age = 51) | | |
|---|---|---|
| | Initial Measurement | Dosage |
| IGF-I | 92 | 4 units/wk 6 dose/day subcutaneously |
| Testosterone Total Free | <22 | 8 mg/day gel |

Patient 1 (Female, Age = 51)

| | Initial Measurement | Dosage |
|---|---|---|
| Progesterone | 0.2 | 200 mg twice/day |
| Estrogen | <16 | 1 mg/daily |
| Melatonin | | |
| DHEA | 23 | 50 mg/day PM |
| Thyroid | 2.2 | 2 grains/day AM |
| Pregnenolone | <10 | 100 mg/day |
| Thymus thymopoietin thymic humoral factor | | 50 mg/twice/day |

Patient 2 (Male, Age = 47)

| | Initial Measurement | Dosage |
|---|---|---|
| IGF-I (HGH) | 46 ng/ml | 4 units/wk 6 dose/day |
| Testosterone | | 30 mg/day gel |
| Total | 517 ng/dl | twice daily |
| Free | 32.0 ng/dl | |
| Progesterone | | |
| Estrogen | | |
| Melatonin | | |
| DHEA | 492 μg/dl | 50 mg/day PM |
| Thyroid | 82 ng/dl | ½ grain/daily AM |
| Pregnenolone | 87 ng/dl | 100 mg/day |
| Thymus | | 2 capsules/day |

Patient 3 (Male, Age = 74)

| | Initial Measurement | Dosage |
|---|---|---|
| IGF-I | 115 ng/ml | 4 units/wk 6 dose/day subcutaneously |
| Testosterone | | 8 mg/day gel |
| Total | 703 ng/dl | |
| Free | 13.3 pg/ml | |
| Progesterone | 0.2 | 200 mg twice/day |
| Estrogen | | |
| Melatonin | 31 pg/ml | 3 ng/day |
| DHEA | 20 | 100 mg/day |
| Thyroid | 5.0 μIU/ml | Armour Thyroid ½ grain/day AM |
| Pregnenolone | <10 | 200 mg/day |
| Thymus | | |

Patient 4 (Male, Age = 54)

| | Initial Measurement | Dosage |
|---|---|---|
| IGF-I | 151 | 4 units/wk 6 dose/day subcutaneously |
| Testosterone | | 60 mg/day gel |
| Total | 51 | |
| Free | 3.1 | |
| Progesterone | | |
| Estrogen | | |
| Melatonin | | |
| DHEA | 298 | |
| Thyroid-Free T | 2.2 | |
| Pregnenolone | 59 | 100 mg/day |
| Thymus | | 50 mg thymic factors (thymosin, thymopoietin & thymic humoral factor) twice daily |

What is claimed is:

1. A hormone replenishment method comprising:
    measuring hormone levels in a sample of an otherwise healthy human subject's blood to determine that the level of human growth hormone and the supplemental hormones selected from the group consisting of sex hormone, melatonin hormone, adrenal hormone, thyroid hormone, and thymus hormone are below pre-determined physiological levels for an adult human; and
    replenishing said level of said deficient hormones to pre-determined physiological levels.

2. The method of claim 1, wherein the step of measuring the level of human growth hormone comprises measuring the level of insulin-like growth factor-I.

3. The method of claim 2, wherein the pre-determined physiological level of human growth hormone is an insulin-like growth factor-I level of 350 μg/mL blood.

4. The method of claim 1, the step of replenishing said level of human growth hormone further comprising a regimen comprising subcutaneous injections of doses of less than 0.5 mg per day.

5. The method of claim 4, wherein said regimen of injections of human growth hormone are administered twice daily.

6. The method of claim 1, wherein said sex hormone comprises at least one of testosterone, progesterone, and estrogen.

7. The method of claim 1, wherein said adrenal hormone comprises dehydroepiandrosterone and pregnenolone.

8. The method of claim 1, the step of measuring a sample of a human subject's blood further comprising determining that each of the supplemental hormones are below pre-determined physiological levels for an adult human.

9. The method of claim 8, wherein the pre-determined physiological level per milliliter of blood of human growth hormone is an insulin-like growth factor-I level of 350 μg, the level of melatonin hormone is 18–69 μg, and the level of thyroid hormone is 150–180 μg.

10. A hormone replenishment method comprising:
    measuring hormone levels in a sample of an otherwise healthy human subject's blood to determine that the level of human growth hormone and at least two of the supplemental hormones selected from the group consisting of sex hormone, melatonin hormone, adrenal hormone, thyroid hormone, and thymus hormone are below pre-determined physiological levels for an otherwise healthy adult human; and
    administering amounts of said deficient hormones to replenish said level of said deficient hormones to pre-determined physiological levels.

11. The method of claim 10, wherein the step of measuring the level of human growth hormone comprises measuring the level of insulin-like growth factor-I.

12. The method of claim 10, wherein the pre-determined physiological level of human growth hormone is an insulin-like growth factor-I level of 350 μg/mL blood.

13. The method of claim 10, the step of administering amounts of human growth hormone further comprising subcutaneous injections of doses of less than 0.5 mg per day.

14. The method of claim 13, wherein said doses are administered twice daily.

15. The method of claim 10, wherein said sex hormone comprises at least one of testosterone, progesterone, and estrogen.

16. The method of claim 10, wherein said adrenal hormone comprises dehydroepiandrosterone and pregnenolone.

17. The method of claim 10, the step of measuring a sample of a human subject's blood further comprising determining that each of the supplemental hormones are below pre-determined physiological levels for an adult human.

18. The method of claim 17, wherein the pre-determined physiological level per milliliter of blood of human growth hormone is an insulin-like growth factor-I level of 350 μg, the level of melatonin hormone is 18–69 μg, and the level of thyroid hormone (T-3) is 150–180 μg.

19. A method of increasing life expectancy and life span comprising:

measuring hormone levels in a sample of an otherwise healthy human subject's blood to determine the level of human growth hormone and at least two of the supplemental hormones selected from the group consisting of sex hormone, melatonin hormone, adrenal hormone, thyroid hormone, and thymus hormone are below pre-determined physiological levels for an adult human; and replenishing said level of human growth hormone and said at least two supplemental hormones to pre-determined physiological levels.

20. The method of claim 19, wherein the step of measuring the level of human growth hormone comprises measuring the level of insulin-like growth factor-I.

21. The method of claim 19, wherein the pre-determined physiological level of human growth hormone is an insulin-like growth factor-I level of 350 μg/mL blood.

22. The method of claim 19, the step of replenishing said level of human growth hormone further comprising establishing a regimen for daily subcutaneous injections of doses of less than 0.5 mg per day administered twice daily.

23. The method of claim 19, wherein said sex hormone comprises at least one of testosterone, progesterone, and estrogen.

24. The method of claim 19, wherein said adrenal hormone comprises dehydroepiandrosterone and pregnenolone.

25. A hormone replenishment kit comprising human growth hormone and at least two of the supplemental hormones selected from the group consisting of sex hormone, melatonin hormone, adrenal hormone, thyroid hormone, and thymus hormone, said human growth hormone and said at least two supplemental hormones present in an amount sufficient in establishing a regimen for the replenishment of said human growth hormone and at least two of said supplemental hormones to predetermined physiological levels.

26. The kit of claim 25, wherein the amount of human growth hormone is provided in intravenous unit form in doses of less than 0.5 mg per day.

27. The kit of claim 26, wherein the amount of human growth hormone is established so that doses of said human growth hormone are administered twice daily.

28. The kit of claim 25, wherein said sex hormone comprises at least one of testosterone, progesterone, and estrogen.

29. The kit of claim 25, wherein said adrenal hormone comprises dehydroepiandrosterone and pregnenolone.

30. A kit for increasing life expectancy and life span comprising human growth hormone and at least two of the supplemental hormones selected from the group consisting of sex hormone, melatonin hormone, adrenal hormone, thyroid hormone, and thymus hormone, said kit for establishing a regimen for the replenishment of said human growth hormone and at least two of said supplemental hormones to predetermined physiological levels.

31. The kit of claim 30, wherein the amount of human growth hormone is provided in intravenous unit form in doses of less than 0.5 mg per day.

32. The kit of claim 31, wherein the amount of human growth hormone is established so that doses of said human growth hormone are administered twice daily.

33. The kit of claim 30, wherein said sex hormone comprises at least one of testosterone, progesterone, and estrogen.

34. The kit of claim 30, wherein said adrenal hormone comprises dehydroepiandrosterone and pregnenolone.

35. A method of inhibiting physiological conditions associated with biological aging comprising:

measuring hormone levels in a sample of an otherwise healthy human subject's blood to determine that the level of human growth hormone and at least two of the supplemental hormones selected from the group consisting of sex hormone, melatonin hormone, adrenal hormone, thyroid hormone (T-3), and thymus hormone are below pre-determined physiological levels for an adult human; and replenishing said level of human growth hormone and said at least two supplemental hormones to pre-determined physiological levels.

36. The method of claim 35, wherein the step of measuring the level of human growth hormone comprises measuring the level of insulin-like growth factor-I.

37. The method of claim 35, wherein the pre-determined physiological level of human growth hormone is an insulin-like growth factor-I level of 350 μg/ml blood.

* * * * *

UNITED STATES PATENT AND TRADEMARK OFFICE
CERTIFICATE OF CORRECTION

PATENT NO.        : 5,855,920
APPLICATION NO.   : 08/766320
DATED             : April 3, 2007
INVENTOR(S)       : Chein It is certified that error appears in the above-identified patent and that said Letters Patent is hereby corrected as shown below:

On Title Page
Item [56], Other Publications, Line #3, please delete "Hypophysectimized" and insert -- Hypophysectomized --.

Item [56], Other Publications, Line #8, please delete --, 1995.--

Signed and Sealed this

Twenty-eighth Day of August, 2007

JON W. DUDAS
*Director of the United States Patent and Trademark Office*

UNITED STATES PATENT AND TRADEMARK OFFICE
CERTIFICATE OF CORRECTION

| | | |
|---|---|---|
| PATENT NO. | : 5,855,920 | Page 1 of 1 |
| APPLICATION NO. | : 08/766320 | |
| DATED | : January 5, 1999 | |
| INVENTOR(S) | : Chein | |

It is certified that error appears in the above-identified patent and that said Letters Patent is hereby corrected as shown below:

On Title Page
Item [56], Other Publications, Line #3, please delete "Hypophysectimized" and insert -- Hypophysectomized --.

Item [56], Other Publications, Line #8, please delete --, 1995.--

This certificate supersedes Certificate of Correction issued August 28, 2007.

Signed and Sealed this

Second Day of October, 2007

JON W. DUDAS
*Director of the United States Patent and Trademark Office*

(12) EX PARTE REEXAMINATION CERTIFICATE (5733rd)
United States Patent
Chein

(10) Number: US 5,855,920 C1
(45) Certificate Issued: Apr. 3, 2007

(54) TOTAL HORMONE REPLACEMENT THERAPY

(75) Inventor: Edmund Y. M. Chein, Beverly Hills, CA (US)

(73) Assignee: Everyoung Technologies, Inc., Palm Springs, CA (US)

Reexamination Request:
No. 90/005,867, Nov. 27, 2000

Reexamination Certificate for:
Patent No.: 5,855,920
Issued: Jan. 5, 1999
Appl. No.: 08/766,320
Filed: Dec. 13, 1996

(51) Int. Cl.
*A61K 35/55* (2006.01)
*A61K 35/26* (2006.01)
*A61K 38/00* (2006.01)
*A61K 31/56* (2006.01)
*A61K 31/405* (2006.01)

(52) U.S. Cl. .................. 424/568; 424/580; 514/21; 514/171; 514/177; 514/178; 514/182; 514/415

(58) Field of Classification Search ................. 514/21, 514/171, 177, 178, 182, 415; 424/568, 580
See application file for complete search history.

(56) References Cited

U.S. PATENT DOCUMENTS

| | | | |
|---|---|---|---|
| 4,791,099 A | 12/1988 | Aroonsakul | |
| 5,407,927 A | 4/1995 | Morales | |
| 5,948,757 A | 9/1999 | Sommer et al. | |

FOREIGN PATENT DOCUMENTS

| | | | |
|---|---|---|---|
| DE | 43 26 948 | * | 12/1995 |
| WO | WO 95/32991 | * | 12/1995 |

OTHER PUBLICATIONS

Scow et al, "Effect of Testosterone Propionate and Growth Hormone on Growth and Chemical Composition of Muscle and Other Tissues in Hypophysectimized Rats", The Endocrine Society, 1965, pp. 852–857, J. B. Lippincott Company.*

Pierpaoli et al, "The Melatonin Miracle, Nature's Age–Reversing Disease Fighting Sex–Enhancing Hormone", The National Academy of Science.*

Klatz, et al., "Can We Grow Young?" Parade Magazine, Apr. 20, 1997, pp. 20–23.

Hodes, "The NIA's Position on Growth Hormone Replacement Therapy in Adults," Journal of American Geriatics Society, 1994, vol. 42, pp. 1208–1211, comments by Edmund Chein, Dec. 1997.

Cranton, et al., "Growth Hormone to Reverse Aging," Alternative Medicine, Jun. 1995, (4 pages).

(Continued)

*Primary Examiner*—Shengjun Wang

(57) ABSTRACT

A hormone replenishment method particularly useful in maintaining the body's neuroendocrine clock at optimal levels and combating conditions associated with advancing age is disclosed. The method includes determining that the level of human growth hormone and at least two other supplemental hormones are below optimal or pre-determined physiological levels for an adult human. Once it has been established that the level of human growth hormone and at least two of certain supplemental hormones are below pre-determined physiological levels, the method includes establishing a regimen for the replenishment of the level of the deficient hormones to optimal or pre-determined physiological levels. The supplements hormones include the sex hormones, namely testosterone, progesterone, and estrogen, the pineal hormone melatonin, the adrenal hormones, namely DHEA and pregnenolone, the thyroid hormone, and the thymus hormone. A method of increasing life expectancy and life span by determining the level of human growth hormone and at least two of the supplemental hormones and establishing a regimen for the maintenance of the level of human growth hormone and supplemental hormones at optimal or pre-determined physiological levels is also disclosed.

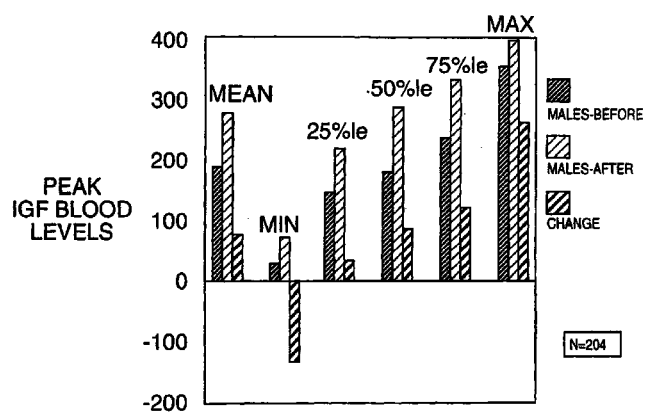

OTHER PUBLICATIONS

"Human Growth Hormone—The Controversy Continues," Muscle & Fitness, Dec. 1995, pp. 262–265.

Klatz, "The War on Aging Has Begun," American Academy of Anti–Aging Medicine.

Rush, "Miraculous hormones so you always have the body of a twenty year old," Cosmopolitan (En Espanol), Aug. 1996 (4 pages).

Klatz, et al. "GH Therapy in 202 Aging Adults," Grow Young with HGH, 1997, 1st edition, pp. 27–35; HarperCollins Publisher, New York, NY.

Carey, "The Latest Anti–Aging Drug is Cheap, Convenient, and Makes You Feel Like a Kid Again. So Why Aren't We All Taking It?" Hippocrates: Health & Medicine for Physicians, Feb. 1996, pp. 69–74.

Lanz, "The Fountain of Youth?" Ability, 1996, vol. 96, Issue 12.

Cranton, et al., "Resetting the Clock," M. Evans and Company, Inc., New York, NY, 1996, pp. 228–233.

Regelson, et al., "The Superhormone Promise, Nature's Antidote to Aging," Simon & Schuster, New York, NY, 1996, pp. 24–27.

Life Extension, Jun. 1997.

Jorgensen, et al., "Three years of growth hormone treatment in growth hormone–deficient adults: near normalization of body composition and physical performance," European Journal of Endocrinology, 1994, pp. 224–228.

Hoffmann, et al., "Growth Hormone Therapy in the Elderly: Implications for the Aging Brain," Pschyc. Endocrinology, vol. 17, No. 4, pp. 327–333, 1992, Pergusson Press Ltd.

Chein, et al., "Life Extension Interview," Nov. 1996, pp. 21–27.

Carey, "The Latest Anti–Aging Drug is Cheap, Convenient, and Makes You Feel Like a Kid Again. So Why Aren't We All Taking It?" Health, Nov.–Dec. 1995, pp. 69–74.

Bengtsson, et al., "Endocrinology and Metabolism," 4th International Meeting on Clinical Research on Growth Hormone Deficiency in Adults, Nov. 1993, Bailliere Tindall, Cannes, France.

Jorgensen, et al., "Beneficial Effects of Growth Hormone Treatment in GH–Deficient Adults," The Lancet, Jun. 3, 1989, pp. 1221–1225.

Christiansen, et al., "GH–Replacement Therapy in Adults," Horm Res, 1991, pp. 66–72, S. Karger AG, Basel, Switzerland.

Christiansen, "The different routes of administration and the effect of hormone replacement therapy on osteoporosis," Fertility and Sterility, 1994 The American Fertility Society, vol. 62 (Suppl. 2), No. 6, Dec. 1994, pp. 152S–156S.

Jorgensen, et al., "Long–term growth hormone treatment in growth hormone deficient adults," Acta Endocrinologica, 1991, pp. 449–453, Copenhagen, Denmark.

Christiansen, et al., "Beneficial effects of GH replacement therapy in adults," Acta Endocrinologica, 1991, pp. 7–13, Copenhagen, Denmark.

Moiler, et al., "Growth hormone dose regimens in adult GH deficiency: effects on biochemical growth markers and metabolic parameters," Clinical Endocrinology, 1993, pp. 403–408, Denmark.

Shoham, et al., "Cotreatment with growth hormone for induction of spermatogenesis in patients with hypogonadtropic hypogonadism," The American Fertility Society, 1992, pp. 1044–1051, vol. 57, No. 5, May 1992.

Cuneo, et al., "Growth hormone treatment in growth hormone–deficient adults. I. Effects on muscle mass and strength," The American Physiological Society, 1991, pp. 688–694.

Morales, et al., "The effect of six months treatment with a 100 mg daily dose of dehydroepiandrosterone (DHEA) on circulating sex steroids, body composition and muscle strength in age–advanced men and women," Clinical Endocrinology, 1998, pp. 421–432, Blackwell Science Ltd.

Bengtsson, et al., "Treatment of Adults with Growth Hormone (GH) Deficiency with Recombinant Human GH," , Journal of Clinical Endocrinology and Metabolism, 1993, pp. 309–317, vol. 76, No. 2.

Cuneo, et al., "Growth Hormone Treatment Improves Serum Lipids and Lipoprotein in Adults With Growth Hormone Deficiency," Metabolism, vol. 42, No. 12, Dec. 1993, pp. 1519–1523.

Parra, et al., "Body Composition in Hypopituitary Dwarfs Before and During Human Growth Hormone Therapy," Metabolism, vol. 28, No. 8, Aug. 1979, pp. 851–857.

Johannsson, et al., "Two Years of Growth Hormone (GH) Treatment Increases Bone Mineral Content and Density in Hypopituitary Patients with Adult–Onset GH Deficiency," Journal of Clinical Endocrinology and Metabolism, 1996, vol. 81, No. 8, pp. 2865–2873.

Gibney, et al., "The Effects of 10 Years of Recombinant Human Growth (GH) in Adult GH–Deficient Patients," The Journal of Clinical Endocrinology & Metabolism, vol. 84, No. 8, 1999, pp. 2596–2602.

Bourguignon, et al., "Pubertal Growth and Final Height in Hypopituitary Boys: A Minor Role of Bone Age at Onset of Puberty," Journal of Clinical Endocrinology and Metabolism, vol. 63, pp. 376–382.

Sartorio, et al., "Growth hormone (GH) treatment in GH–deficient adults: effects on muscle size, strength and neural activation," Clinical Physiology 1994, pp. 527–537.

Coope, "Tailoring HRT to the patient's need," The Practitioner, Jun. 1991, vol. 235, pp. 483–486.

Cuneo, et al., "Growth hormone treatment in growth hormone–deficient adults. II. Effects on exercise performance," The American Physiological Society, 1991, pp. 695–700.

Pierpaoli, et al., "The Melatonin Miracle, Nature's Age–Reversing Disease Fighting Sex–Enhancing Hormone," The National Academy of Science, 1995.

Regelson, et al., "The Super–Hormone Promise," 1996 Pocket Books, New York, NY.

Chein, "Control the Aging Process Through Age Reversal," 1997.

Papadakis, et al., "Growth Hormone Replacement in Healthy Older Men Improves Body Composition but Not Functional Ability," American College of Physicians; Annals of Internal Medicine, vol. 124, No. 8, Apr. 15, 1996, pp. 708–717.

Chung, et al., "Growth hormone replacement therapy in Adults with growth hormone deficiency; thrice weekly low dose administration," Journal of Korean Medical Science, vol. 9, No. 2, Apr. 994, pp. 169–178.

Holloway, et al., "Effects of Recombinant Human Growth Hormone on Metabolic Indices, Body Composition, and Bone Turnover in Healthy Elderly Women," Journal of Clinical Endocrinology and Metabolism, vol. 79, No. 2, 1994, pp. 470–479.

Reznick, et al., "Effects of Growth Hormone on Skeletal Muscles of Aging Systems," Age, vol. 19, 1996, pp. 39–44.

Bengtsson, et al. "Treatment of Adults with Growth Hormone (GH) Deficiency with Recombinant Human GH," Journal of Clinical Endocrinology and Metabolism, vol. 76, No. 2, 1993, pp. 309–317.

Morales, et al., "Effects of Replacement Dose of Dehydroepiandrosterone in Men and Women of Advancing Age," Journal of Clinical Endocrinology and Metabolism, vol. 78, No. 6, 1994, pp. 1360–1367.

Haimov, et al., "Potential of Melatonin Replacement Therapy in Older Patients with Sleep Disorders," Drugs & Aging 7 (2), 1995, pp. 75–78, Adis International Limited, Auckland, New Zealand.

Broda O. Barnes, M.D. Research Foundation, Inc., Women's International Pharmacy Lecture, Feb. 1992, Trumbull, CT.

The Tenth Annual International Symposium on Man and His Environment in Health and Disease, Feb.–Mar. 1992, Dallas, TX.

Broda O. Barnes Research Foundation, Inc., Physicians Teaching Seminar, Mar. 1996, Seattle, WA.

American Academy of Anti–Aging Medicine International Conference, Jun. 1996, Madrid, Spain.

The American Academy of Anti–Aging Medicine Conference on the Future of Healthcare, Dec. 1996, Las Vegas, NV.

The Merck Index, An Encyclopedia of Chemicals, Drugs, and Biologicals, 12th Ed., 1996, pp. 630–632, 941, 991, 1149–50 1323, 1328, 1335–36, 1487–88, 1569, 1604–06, Whitehouse Station, NJ.

"Growth Hormone Therapy in Aging Adults: Place and Dosage in a Multiple Hormonal Replacement Therapy," 1996(?).

Hertoghe, T., "Chapter 3: Growth Hormone Therapy in Aging Adults," pp. 10–28, 1996(?).

* cited by examiner

EX PARTE REEXAMINATION CERTIFICATE ISSUED UNDER 35 U.S.C. 307

THE PATENT IS HEREBY AMENDED AS INDICATED BELOW.

AS A RESULT OF REEXAMINATION, IT HAS BEEN DETERMINED THAT:

The patentability of claims 1–24, 29, 34–37 is confirmed.

Claims 25–28 and 30–33 are cancelled.

\* \* \* \* \*